United States Patent
Dekker

(10) Patent No.: US 7,001,337 B2
(45) Date of Patent: Feb. 21, 2006

(54) MONITORING PHYSIOLOGICAL PARAMETERS BASED ON VARIATIONS IN A PHOTOPLETHYSMOGRAPHIC SIGNAL

(75) Inventor: Andreas Lubbertus Aloysius Johannes Dekker, Maastricht (NL)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/790,950

(22) Filed: Mar. 2, 2004

(65) Prior Publication Data

US 2004/0260186 A1    Dec. 23, 2004

Related U.S. Application Data

(63) Continuation-in-part of application No. 10/081,719, filed on Feb. 22, 2002, now Pat. No. 6,702,752, which is a continuation-in-part of application No. 10/081,887, filed on Feb. 22, 2002, now Pat. No. 6,805,673, which is a continuation-in-part of application No. 10/081,165, filed on Feb. 22, 2002, now Pat. No. 6,896,661, which is a continuation-in-part of application No. 10/081,168, filed on Feb. 22, 2002, now Pat. No. 6,709,402.

(51) Int. Cl.
*A61B 5/02* (2006.01)

(52) U.S. Cl. ............ 600/484; 600/483; 600/500; 600/507

(58) Field of Classification Search ........ 600/529–543, 600/500–505, 507, 481, 483–485
See application file for complete search history.

(56) References Cited

U.S. PATENT DOCUMENTS

| | | |
|---|---|---|
| 3,704,706 A | 12/1972 | Herczfeld et al. |
| 4,306,567 A | 12/1981 | Krasner |
| 4,379,460 A | 4/1983 | Judell |
| 4,404,974 A | 9/1983 | Titus |
| 4,510,944 A | 4/1985 | Porges .................. 128/687 |
| 4,765,340 A | 8/1988 | Sakai et al. |
| 4,777,960 A | 10/1988 | Berger et al. ............ 128/706 |
| 4,781,201 A | 11/1988 | Wright et al. |
| 4,813,427 A | 3/1989 | Schlaefke et al. ........ 128/671 |
| 4,858,638 A | 8/1989 | Cseri ....................... 137/115 |
| 4,860,759 A | 8/1989 | Kahn et al. ............... 128/668 |
| 4,863,265 A | 9/1989 | Flower et al. |
| 4,869,254 A | 9/1989 | Stone et al. |
| 4,884,578 A | 12/1989 | Morgenstern |
| 4,899,760 A | 2/1990 | Jaeb et al. ................ 128/696 |
| 4,930,517 A | 6/1990 | Cohen et al. ............. 128/671 |

(Continued)

*Primary Examiner*—Robert L. Nasser
*Assistant Examiner*—Navin Natnithithadha
(74) *Attorney, Agent, or Firm*—Marsh Fischmann & Breyfogle LLP

(57) ABSTRACT

A method and apparatus are disclosed for using photoplethysmography to obtain physiological parameter information related to respiration rate, heart rate, heart rate variability, blood volume variability and/or the autonomic nervous system. In one implementation, the process involves obtaining (2502) a pleth, filtering (2504) the pleth to remove unwanted components, identifying (2506) a signal component of interest, monitoring (2508) blood pressure changes, monitoring (2510) heart rate, and performing (2512) an analysis of the blood pressure signal to the heart rate signal to identify a relationship associated with the component of interest. Based on this relationship, the component of interest may be identified (2514) as relating to the respiration or Mayer Wave. If it is related to the respiration wave (2516), a respiratory parameter such as breathing rate may be determined (2520). Otherwise, a Mayer Wave analysis (2518) may be performed to obtain parameter information related to the autonomic nervous system.

13 Claims, 26 Drawing Sheets

U.S. PATENT DOCUMENTS

| | | | |
|---|---|---|---|
| 4,958,638 A | 9/1990 | Sharpe et al. | |
| 4,960,129 A | 10/1990 | DePaola et al. | 128/695 |
| 4,972,842 A | 11/1990 | Korten et al. | 128/716 |
| 5,033,472 A | 7/1991 | Sato et al. | 128/691 |
| 5,078,136 A | 1/1992 | Stone et al. | |
| 5,111,817 A | 5/1992 | Clark et al. | |
| 5,170,794 A | 12/1992 | Reiche | |
| 5,273,036 A | 12/1993 | Kronberg et al. | 128/633 |
| 5,368,224 A | 11/1994 | Richardson et al. | |
| 5,385,144 A | 1/1995 | Yamanishi et al. | |
| 5,396,893 A | 3/1995 | Oberg et al. | |
| 5,423,322 A | 6/1995 | Clark et al. | |
| 5,431,159 A | 7/1995 | Baker et al. | |
| 5,482,036 A | 1/1996 | Diab et al. | |
| 5,490,505 A | 2/1996 | Diab et al. | |
| 5,511,553 A | 4/1996 | Segalowitz | 128/696 |
| 5,553,615 A | 9/1996 | Carim et al. | |
| 5,555,882 A | 9/1996 | Richardson et al. | |
| 5,575,284 A | 11/1996 | Athan et al. | |
| 5,623,933 A | 4/1997 | Amano et al. | |
| 5,755,229 A | 5/1998 | Amano et al. | |
| 5,766,127 A | 6/1998 | Pologe et al. | |
| 5,776,071 A | 7/1998 | Inukai et al. | |
| 5,813,989 A * | 9/1998 | Saitoh et al. | 600/484 |
| 5,830,137 A | 11/1998 | Scharf | |
| 5,842,979 A | 12/1998 | Jarman | 600/322 |
| 5,853,364 A | 12/1998 | Baker, Jr. et al. | |
| 5,862,805 A | 1/1999 | Nitzan | |
| 5,865,167 A | 2/1999 | Godik | |
| 5,865,756 A | 2/1999 | Peel, III | |
| 5,885,213 A | 3/1999 | Richardson et al. | |
| 5,902,235 A | 5/1999 | Lewis et al. | 600/323 |
| 5,919,134 A | 7/1999 | Diab | 600/323 |
| 5,931,779 A | 8/1999 | Arakaki et al. | 600/310 |
| 5,934,277 A | 8/1999 | Mortz | 128/633 |
| 5,954,644 A | 9/1999 | Dettling et al. | 600/322 |
| 5,971,930 A | 10/1999 | Eighazzawi | 600/483 |
| 5,980,463 A | 11/1999 | Brockway et al. | 600/485 |
| 5,993,893 A | 11/1999 | Kikuchi | 427/8 |
| 5,997,482 A | 12/1999 | Vaschillo et al. | 600/484 |
| 6,011,985 A | 1/2000 | Athan et al. | 600/322 |
| 6,027,455 A | 2/2000 | Inukai et al. | 600/490 |
| 6,028,311 A | 2/2000 | Sodickson et al. | 250/343 |
| 6,064,910 A | 5/2000 | Andersson et al. | 607/20 |
| 6,067,462 A | 5/2000 | Diab et al. | 600/310 |
| 6,081,742 A | 6/2000 | Amano et al. | 600/513 |
| 6,099,481 A | 8/2000 | Daniels et al. | 600/538 |
| 6,129,675 A | 10/2000 | Jay | 600/485 |
| 6,155,992 A | 12/2000 | Henning et al. | 600/583 |
| 6,325,761 B1 * | 12/2001 | Jay | 600/485 |
| 6,480,733 B1 | 11/2002 | Turcott | 600/516 |
| 6,662,032 B1 * | 12/2003 | Gavish et al. | 600/323 |
| 6,702,752 B1 | 3/2004 | Dekker | |
| 6,709,402 B1 | 3/2004 | Dekker | |
| 6,805,673 B1 | 10/2004 | Dekker | |
| 2003/0163050 A1 | 8/2003 | Dekker | |

* cited by examiner

MONITORING PHYSIOLOGICAL PARAMETERS BASED ON VARIATIONS IN A PHOTOPLETHYSMOGRAPHIC SIGNAL

CROSS-REFERENCE TO RELATED APPLICATIONS

This application is a continuation-in-part of the following applications: U.S. patent application Ser. No. 10/081,719, which is entitled "Monitoring Respiration Based on Plethysmographic Heart Rate Signal," which was filed on Feb. 22, 2002, now U.S. Pat. No. 6,702,752; U.S. patent application Ser. No. 10/081,887, which is entitled "Monitoring Mayer Wave Effects Based on a Photoplethysmographic Signal," which was filed on Feb. 22, 2002, now U.S. Pat. No. 6,805,673; U.S. patent application Ser. No. 10/081,165, which is entitled "Monitoring Physiological Parameters Based on Variations in a Photoplethysmographic Baseline Signal," which was filed on Feb. 22, 2002, now U.S. Pat. No. 6,896,661; and U.S. patent application Ser. No. 10/081,168, which is entitled "Apparatus and Method for Monitoring Respiration with a Pulse Oximeter," which was filed on Feb. 22, 2002, now U.S. Pat. No. 6,709,402, the entire disclosures of which are incorporated by reference in their entirety herein.

FIELD OF THE INVENTION

The present invention relates, in general, to the noninvasive monitoring of physiological parameters such as respiration rate or low frequency heart rate/blood volume variability based on optical (visible and/or non-visible spectrum) signals and, in particular, to monitoring such parameters based on the processing of received optical signals to distinguish effects related to the patient's respiratory system and/or autonomic nervous system. The invention can be readily implemented in connection with pulse oximetry instruments so as to expand the utility of such instruments.

BACKGROUND OF THE INVENTION

Photoplethysmography relates to the use of optical signals transmitted through or reflected by a patient's blood, e.g., arterial blood or perfused tissue, for monitoring a physiological parameter of a patient. Such monitoring is possible because the optical signal is modulated by interaction with the patient's blood. That is, interaction with the patient's blood, generally involving a wavelength and/or time dependent attenuation due to absorption, reflection and/or diffusion, imparts characteristics to the transmitted signal that can be analyzed to yield information regarding the physiological parameter of interest. Such monitoring of patients is highly desirable because it is noninvasive, typically yields substantially instantaneous and accurate results, and utilizes minimal medical resources, thereby proving to be cost effective.

A common type of photoplethysmographic instrument is the pulse oximeter. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of a patient's pulse cycle, information can be obtained regarding blood oxygen saturation.

The algorithms for determining blood oxygen saturation related values are normally implemented in a digital processing unit. Accordingly, one or more analog to digital (A/D) converters are generally interposed between the detector and the digital processing unit. Depending on the specific system architecture employed, a single multi-channel digital signal may be received by the digital processing unit or separate digital signals for each channel may be received. In the former case, the digital processing unit may be used to separate the received signal into separate channel components. Thus, in either case, the digital processing unit processes digital information representing each of the channels. Such information defines input digital photoplethysmographic signals or digital "pleths." These pleths generally contain two components. The first component of interest is a low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component, sometimes termed the "AC component," generally corresponds to the change in attenuation due to the pulsation of the blood. In general, the AC component represents a varying waveform which corresponds in frequency to that of the heartbeat. In contrast, the DC component is a more steady baseline component, since the effective volume of the tissue under investigation varies little or at a low frequency if the variations caused by the pulsation of the heart are excluded from consideration.

Pulse oximeters typically provide as outputs blood oxygen saturation values and, sometimes, a heart rate and a graphical representation of a pulsatile waveform. The information for generating each of these outputs is generally obtained from the AC component of the pleth. In this regard, some pulse oximeters attempt to filter the DC component from the pleth, e.g., in order to provide a better digitized AC component waveform. Other pulse oximeters may measure and use the DC component, e.g., to normalize measured differential values obtained from the AC component or to provide measurements relevant to motion or other noise corrections. Generally, though, conventional pulse oximeters do not monitor variations in the DC component of a pleth or pleths to obtain physiological parameter information in addition to the outputs noted above.

SUMMARY OF THE INVENTION

The present invention is directed to using photoplethysmography to obtain physiological information related to respiration or the autonomic nervous system based on analysis of pleth characteristics separate from or in addition to the AC component or pulsatile waveform. The invention thus provides important diagnostic or monitoring information noninvasively. Moreover, various aspects of the invention can be implemented using one or more channels of a conventional pulse oximeter, thereby providing additional functionality to instruments that are widely available and trusted, as well as providing access to important information for treatment of patients on a cost-effective basis.

In a preferred implementation, the present invention obtains information regarding a physiological parameter based on analysis of the DC component of the pleth ("pleth baseline signal") to distinguish an effect related to the autonomic nervous system from an effect related to the respiratory system. It has been recognized that the pleth baseline signal can be analyzed to yield important information in this regard. In particular, it has been recognized that the pleth baseline signal includes at least three principal components: 1) a component related to respiration or the "respiration wave", 2) a low frequency component associated with the autonomic nervous system or vaso motor center, sometimes termed the "Mayer Wave", and 3) a very low frequency component which is associated with temperature control. Regarding the second of these, the origin and nature of the Mayer Wave is not fully settled. For present purposes, the Mayer Wave relates to a low frequency variation in blood pressure, heart rate, and/or vaso constriction.

The first two components noted above have particular significance for diagnostic and patient monitoring purposes. In particular, the amplitude and frequency of the Mayer Wave are seen to change in connection with hypertension, sudden cardiac death, ventricular tachycardia, coronary artery disease, myocardial infarction, heart failure, diabetes, and autonomic neuropathy and after heart transplantation. Respiration rate is monitored during a variety of medical procedures, for example, as an indication of a patient's stress levels and to identify patient respiratory distress. The present invention is based, in part, on the recognition that effects related to these components can be monitored based on analyzing a pleth to identify physiological parameter information. In particular, it is expected that both the Mayer and respiration waves influence heart rate (and related parameters such as variations in blood pressure and blood volume) by direct influence on the vaso motor center. In the latter case, this is by a "spillover" from the breathing center to the vaso motor center, which increases heart rate during inspiration.

A difficulty associated with obtaining physiological parameter information based on the Mayer Wave and the respiration wave relates to distinguishing the effects associated with these waves, particularly in view of the fact that each of these waves can occur within overlapping frequency ranges. In accordance with the present invention, physiological parameter information is obtained by distinguishing these two pleth components in any of various ways. These generally include distinguishing the waves based on frequency, based on a wave characteristic other than frequency and based on-information not directly derived from Mayer/respiration wave comparison. With regard to distinguishing the waves based on frequency, as noted above, the Mayer Wave and respiration wave may occur in overlapping frequency bands. Accordingly, a process for distinguishing those waves based on frequency may be assisted by modifying one or both of these wave frequencies to create a cognizable basis of distinction. In some cases, this can be accomplished by controlling or having the patient control his respiration rate.

Alternatively, the waves may be distinguished based on a wave characteristic other than frequency such as waveform or phase. In the latter regard, it has been recognized that the respiration and Mayer waves may influence blood pressure by a change in heart rate and vasoconstriction. Respiration, however, causes a change in blood pressure because of thoracic pressure differences during inspiration and expiration. Inspiration causes a decrease in left ventricular filling, decreasing the blood pressure. Accordingly, during inspiration blood pressure drops and heart rate rises. In contrast, in the rising part of the Mayer Wave, both blood pressure and heart rate are increased simultaneously. Therefore, blood pressure and heart rate changes will be out of phase if they are caused by respiration, while in a Mayer Wave they are in phase.

The Mayer and respiration waves may also be distinguished based on information not directly derived from Mayer/respiration wave comparison. For example, increases in blood oxygen levels over a predetermined frequency range may be correlated with known physiological effects caused by respiration. More particularly, increases in the ratio of oxygenated hemoglobin over deoxygenated hemoglobin over a frequency of 0 to 0.5 Hz (or frequencies of 1 Hz or greater in the case of neonates) may be caused due to inspiration, which has the effect of lowering the amount of venous blood in the tissue and thus increases the ratio of arterial blood to venous blood in the tissue. Such effects may be indicated, for example, by monitoring pleths associated with multiple channels to identify variations in blood oxygenation within the relevant frequency bands. It will be appreciated that this allows for distinguishing an effect associated with the respiration wave without directly separating or otherwise comparing a respiration wave component and a Mayer Wave component.

Once an effect is associated with one of the respiration wave and the Mayer Wave has been distinguished, this can be used to obtain physiological parameter information. Depending on the specific implementation, as discussed above, the waves may be distinguished based on a known characteristic of one of the waves, a known difference between the waves, or a secondary effect associated with one of the waves. In cases where the waves are distinguished based on a known characteristic or secondary effect of one of the waves, the physiological parameter information may be derived from the wave having the known characteristic or secondary effect, from the other wave, or from a signal including both wave components.

In accordance with one aspect of the present invention, a method is provided for monitoring a physiological parameter of a patient. The method includes the steps of obtaining a pleth that includes at least a first component associated with the operation of the patient's respiratory system and a second component associated with the patient's autonomic nervous system, processing the pleth to distinguish an effect associated with one of the first and second components from an effect associated with the other of the components, and using this distinguished effect to monitor the physiological parameter. Depending on the specific implementation, this step of obtaining a pleth may involve obtaining information corresponding to a single channel of transmitted light (visible and/or nonvisible spectrum) or multiple channels. For example, the invention may be implemented in connection with a conventional pulse oximeter that provides at least two separate channels and corresponding pleths. One or both of these pleths may be utilized in monitoring the physiological parameter of interest. The step of processing the pleth may involve distinguishing a Mayer Wave effect from a respiration wave effect, for example, in any of the ways discussed above. The physiological parameter monitored may be a respiratory parameter such as respiration rate or a Mayer Wave parameter such as low frequency heart rate variations or blood volume variations. An associated apparatus includes a port for receiving the pleth and a processor operative for processing the pleth signal to distinguish effects associated with the first and second components. A system incorporating such an apparatus may include one or more transmitters for transmitting an optical signal, and a detector signal for detecting the transmitted optical signals and providing the pleth based thereon.

In accordance with another aspect of the present invention, a method is provided for monitoring a patient's breathing. The method involves the steps of transmitting an optical signal relative to a patient such that the signal interacts with perfused tissue of the patient, operating a detector system to detect the transmitted optical signal and provide a pleth reflective of the detected optical signal, where the pleth includes at least a first component associated with the patient's respiratory system and a second component associated with the patient's autonomic nervous system, processing the pleths to distinguish an effect associated with the first component from effects associated with the second component and using the distinguished effect to monitor the patient's breathing. In one implementation, a respiratory effect is distinguished from an autonomic nervous system effect based on a phase difference between the associated waves. In particular, blood pressure and heart rate changes will have one phase relationship if they are caused by respiration and another phase relationship if they are associated with a Mayer Wave. Thus, by acquiring both the changes in blood pressure and heart rate, the phase relationship can be determined to distinguish effects associated with the respiration wave from effects associated with the Mayer Wave. This information is then used to identify pleth characteristics associated with respiration which are, in turn, monitored to determine the respiration rate.

In another aspect of the present invention, a method is provided to monitor at least one secondary physiological process through variations caused by that process in at least a portion of an optical signal used to calculate a value related to blood oxygenation levels. The method comprises the steps of applying electromagnetic radiation of one or more known wavelengths to a portion of tissue, detecting the intensity of the electromagnetic radiation relative to that portion of tissue, generating at least a first signal indicative of the detected radiation, processing this signal(s) such that at least a first value related to blood oxygen levels is produced, and monitoring this first value over a predetermined time to identify variations indicative of a secondary physiological process. Finally, the method includes generating an output signal indicative of the secondary physiological process.

Processing may comprise using a portion of the detected signal(s) for producing a first value related to blood oxygen levels. In particular, the detected signal(s) may be filtered to isolate discrete portions of the signal. Once the signals are filtered, values may be monitored in each of the discrete signal portions such that a first blood oxygen related value may be determined. Once a first value is determined, it may be monitored for variations known to be associated with a secondary process such as a cardiopulmonary process. For example, in the case where the first value is a patient's $HbO_2/Hb$ ratio, an increase in the ratio over a known time period may be indicative of respiration. As will be appreciated, if a variation caused by respiration is identified in the ratio an output may be generated indicative of respiration.

In another aspect of the present invention, an apparatus is provided for monitoring respiration using optical signals to identify changes caused by the respiration in values related to blood oxygen levels. The apparatus comprises an emitter for emitting first and second wavelengths of the electromagnetic radiation to a portion of living tissue, a detector for detecting the first and second wavelengths of electromagnetic radiation as applied to the tissue and for producing a detector output signal indicative thereof, and a processor. The processor is operative for filtering the detector signal such that individual portions of the detector signal may be isolated. The processor is configured to determine a value related to blood oxygen levels in the monitored tissue through mathematical computation using at least a first portion of each filtered signal. Once the blood oxygen related value is determined for the tissue, it may be intermittently, periodically or substantially continuously monitored to determine increases and decreases which are indicative of the patient's respiration. Finally, upon determining changes, in the blood value indicative of respiration, the processor may generate an output signal showing a patient's respiration frequency.

The detector output signals may be received by the processor and an associated filtering module, such that one or more portions of each signal may be isolated. For example, if the detection signals contain both an AC and DC component, the filtering module may be operable to remove and/or isolate either the AC or DC component. Additionally, the filter may comprise a band-pass filter which is capable of isolating portions of the detected signals according to frequency. As will be appreciated, the AC component is typically a higher frequency component than the DC component, therefore a high-pass filter may be used to remove the AC component from the detected signal.

The processor may be further configured to determine blood analyte values related to the blood oxygen levels of the monitored tissue through a mathematical computation using at least a first portion of the first filtered signal and a first portion of the second filtered signal. For example, the processor may be configured such that it is able to determine values related to the Ratio of Ratios that is conventionally used in determining oxygen saturation levels. As will be appreciated, by using the filtered signals which may only contain a DC or AC component, the oxygen saturation level determined will be related only to that component. For example, the DC component of the detected electromagnetic signal represents the detected portion of the electromagnetic radiation as applied to the tissue as a whole where the AC portion represents the variation in volume in that portion of tissue due to variation in blood volume caused by the pulse. Therefore, by using the DC signal, the blood analyte values in the tissue independent of the pulsatile AC component may be determined.

Once the blood oxygen analyte related values are determined for the desired component (e.g., AC or DC) of the detected signals, this value may be monitored for increases and decreases indicative of respiration. For example, increases in blood oxygen levels over a predetermined frequency range may be correlated with known physiological effects caused by respiration. More particularly, increases in the ratio of oxygenated hemoglobin over deoxygenated hemoglobin over a frequency of 0 to 0.5 hertz may be caused due to inspiration (breathing in), which has the effect of lowering the amount of venous blood in the tissue and thus increases the ratio of arterial (oxygenated) blood to deoxygenated blood in the tissue.

In accordance with another aspect of the present invention, a method is provided for monitoring a Mayer Wave effect, such as a low frequency variation in blood pressure, heart rate, blood volume and/or vasoconstriction. The method involves obtaining a pleth signal that is modulated based on interaction of a transmitted optical signal with a patient's blood (e.g., arterial blood and/or perfused tissue), processing the pleth signal to identify an effect related to the Mayer Wave, and providing an output related to the Mayer Wave effect (e.g., a waveform, one or more values or other information, e.g., related to the amplitude and/or period/ frequency of the Mayer Wave or variations therein). This method may be implemented in connection with a conventional pulse oximeter. In this regard, the step of obtaining a pleth signal may involve operating the pulse oximeter to transmit optical signals relative to the patient and provide a detector signal representative of the received optical signals and accessing at least a portion of the detector signal corresponding to one or more channels of the transmitted optical signals. For example, the oximeter may be operated to transmit single or multiple channel (e.g., red and infrared channels) signals. In either case, the detector signal will generally include a pleth signal. In the case of a multiple channel detector signal, each channel will generally include a pleth signal and information regarding one channel may be accessed in accordance with the present invention, or information regarding multiple channels may be used, e.g., by combining the channel signals.

Once the pleth is obtained, it may be processed in a variety of ways to identify a Mayer Wave effect of interest. In one implementation, such processing involves frequency based filtering to identify the effect of interest. In particular, a signal or series of values representing or otherwise based on the obtained pleth signal is filtered to selectively pass a spectral peak located between about 0.05 Hz and 0.5 Hz. The lower end of this range may be selected to eliminate at least a substantial portion of spectral power related to the very low frequency peak noted above associated with temperature control. The upper end of the noted range may be selected in conjunction with controlling the patient's respiration rate. In this regard, 0.5 Hz will allow for separation of the Mayer Wave from the respiration wave for many applications. A filtering range of between about 0.08–0.2 may be preferred for isolation of the Mayer Wave from the noted, potentially interfering spectral peaks. More preferably, because the Mayer Wave is generally found within a narrow frequency band at about 0.1 Hz, a narrow band pass filter may be utilized having a nominal pass band width (designated in conventional fashion) of no more than about 0.05 Hz and including within such pass band (preferably substantially centered relative thereto) or the frequency 0.1 Hz. Such filtering generally enables identifying a Mayer Wave effect from the signal under analysis.

In accordance with another aspect of the present invention, a low frequency blood volume variation of a patient is monitored. The associated method involves obtaining a pleth signal (e.g., as described above), processing the pleth signal to obtain information regarding a low frequency blood volume variation of the patient, and monitoring the low frequency blood volume variation over time to identify a characteristic of interest for patient monitoring or diagnostic purposes. The low frequency blood volume variation generally relates to a spectral peak of the pleth signal located between about 0.05 Hz and 0.5 Hz. Thus, the obtained pleth signal may be band pass filter, as discussed above, to extract information regarding the noted blood variability. Because such low frequency blood volume variability is related to the Mayer Wave, changes in its amplitude and/or frequency may have diagnostic significance as noted above.

In accordance with a further aspect of the present invention, a low frequency heart rate variability of a patient is monitored. The associated method involves obtaining a pleth signal, analyzing the pleth signal to obtain heart rate information, analyzing the heart rate information to obtain information regarding heart rate variability information, and monitoring the heart rate variability information to identify a characteristic of interest. The resulting heart rate variability information may be monitored, for example, to identify Mayer Wave phenomena of potential diagnostic significance.

The step of obtaining a pleth signal generally involves receiving a digital signal representative of an optical signal modulated based on interaction with perfused tissue of a patient. Such a signal may be provided using components of a conventional pulse oximeter. Pulse oximeters typically transmit red and infrared signals, thereby yielding red and infrared pleths. Either or both of these pleths may be utilized in accordance with the present invention. In particular, each of these pleths generally has a fundamental frequency corresponding to the patient's heart rate. Accordingly, either pleth can be used to yield the desired heart rate information. In general, for normally oxygenated patients, the infrared channel typically has the stronger pleth waveform and may be preferred for heart rate calculations. For poorly oxygenated patients, the red pleth may be preferred. In many cases, a combination of the two signals may provide a better waveform for heart rate analysis than either signal alone.

The pleth may be processed to obtain heart rate information in a variety of ways. As noted above, the pleth is generally a periodic signal having a fundamental frequency corresponding to the patient's heart rate. Accordingly, heart rate may be determined by performing peak-to-peak measurements on the pleth to determine the pulse period and, hence, pulse frequency. For example, such maxima may be obtained by identifying a change in sign of differential values between successive samples or groups of samples along the pleth or of a function fitted to the pleth. Alternatively, other points on the waveform, such as nominal zero (or average pleth value) crossings may be monitored. Such zero crossings would be expected to have a frequency of twice the heart rate. Such period measurements can be complicated due to the typically noisy waveform of the pleths. Accordingly, multiple waveforms may be utilized.

Additionally, the heart rate calculations may be performed in the frequency domain. In this regard, a processor may be configured to obtain a Fourier transform of the pleth. Once the Fourier transform is obtained, the pulse rate can be identified as the fundamental frequency of the pleth corresponding to the patient's heart rate. In any case, once the heart rate is determined, it can be monitored to identify low frequency variations of interest. In particular, oscillatory variations having a frequency associated with the Mayer Wave, as discussed above, may be monitored for diagnostic purposes. For example, in one embodiment oscillatory variations having a frequency of between about 0.15 and 0.5 Hz and, especially, between about 0.2 and 0.4 Hz, are monitored for identifying respiration rate. In a further embodiment, this range may be expanded to 0–5 Hz to accommodate the higher respiration rates of newborns.

One or more filters may be used in obtaining heart rate variability information based on a pleth signal in accordance with the present invention. In this regard, an adaptive filter may be used to track the fundamental frequency of the pleth and, hence, the patient's pulse rate. For example, such a filter may function as a narrow band pass filter having a band pass that is centered on the fundamental frequency of the pleth. The transfer function of the filter may be varied, e.g., based on analysis of successive waveforms, to track the potentially changing fundamental frequency. The filter or associated logic may thus be adapted to output a time series of pulse rate values. Such a time series of pulse rate values, whether obtained as an output of an adaptive filter system or otherwise, may be filtered using an adaptive filter that tracks a selected spectral peak of the time series to provide an output related thereto. Such filtering provides a fast, robust and computationally efficient mechanism for noninvasively monitoring low frequency heart rate variability based on pleth signals.

In accordance with another aspect of the present invention, a pleth signal is analyzed to identify a heart rate variability parameter associated with respiration rate. The associated process involves obtaining a pleth signal, processing the pleth signal to obtain heart rate samples, monitoring the heart rate samples to identify a heart rate variability, and determining a respiration rate based on the heart rate variability. It is known that heart rate varies with the respiration cycle, an effect called Respiratory Sinus Arrhythmia. The present invention provides a robust process for monitoring this effect and determining respiration rate based on pleth signals. A novel processor and pulse oximeter incorporating such processing are also provided in accordance with the present invention.

According to a still further aspect of the present invention, a method is provided for monitoring a patient using a pleth instrument. The method involves configuring a pleth instrument relative to the patient for a pleth analysis, e.g., by attaching a probe to the patient, causing a respiration rate of the patient to be at least at a given threshold, operating the instrument to obtain a pleth signal, and operating the instrument to process the pleth signal to identify an effect related to the Mayer Wave and provide an output related thereto. As noted above, the Mayer Wave generally has a frequency of about 0.1 Hz. Accordingly, the threshold is preferably greater than 0.1 Hz, for example, at least about 0.167 Hz or 10 breaths a minute. In this regard, the patient's respiration rate may be controlled, e.g., using a respirator, or the patient may be instructed to control his breathing. The pleth instrument may be operated to obtain a single or multi-channel pleth signal and one or more such channels may be processed to identify any suitable pleth effect such as low frequency variations in blood volume, pulse rate, blood pressure or vasoconstriction. Information relating to the effect of interest may be output as discussed above. Such use of a pleth instrument in conjunction with frequency controlled patient breathing allows for convenient monitoring of Mayer Wave effects.

An apparatus in accordance with the present invention includes an input port for receiving a pleth signal, a processor for processing the pleth signal to identify an effect related to the Mayer Wave and an output port for providing output information relating to the effect of interest. For example, the input port may be adapted for receiving a cable connected to a probe or may be a processor module configured to access a digital signal, and the output port may be a port configured to interface with an external monitor or other display device or may be a processor module configured to provide access to the output information in digital form. The processor preferably includes a filter for use in extracting information regarding the Mayer Wave effect directly from the pleth signal or from processed information obtained therefrom. For example, the pleth signal may be filtered to obtain low frequency blood volume variation information, or the pleth signal may be processed to provide heart rate information and this information may be filtered to yield low frequency heart rate variability information. The apparatus may be incorporated into a conventional pleth instrument such as a pulse oximeter. In this manner, the functionality of pulse oximeters may be advantageously extended.

The present invention thus allows pleths to be analyzed to monitor physiological parameters related to operation of the respiration system and/or the autonomic nervous system. Such parameters can be monitored noninvasively based on one or more channels of optical signals transmitted relative to a patient. The invention can be implemented in connection with conventional pulse oximetry components so as to expand the functionality of such instruments as well as to provide important physiological parameter information in a cost effective manner.

BRIEF DESCRIPTION OF THE DRAWINGS

For a more complete understanding of the present invention and further advantages thereof, references now made to the following detailed description, taken in conjunction with the drawings, in which.

DETAILED DESCRIPTION

Figure 1:
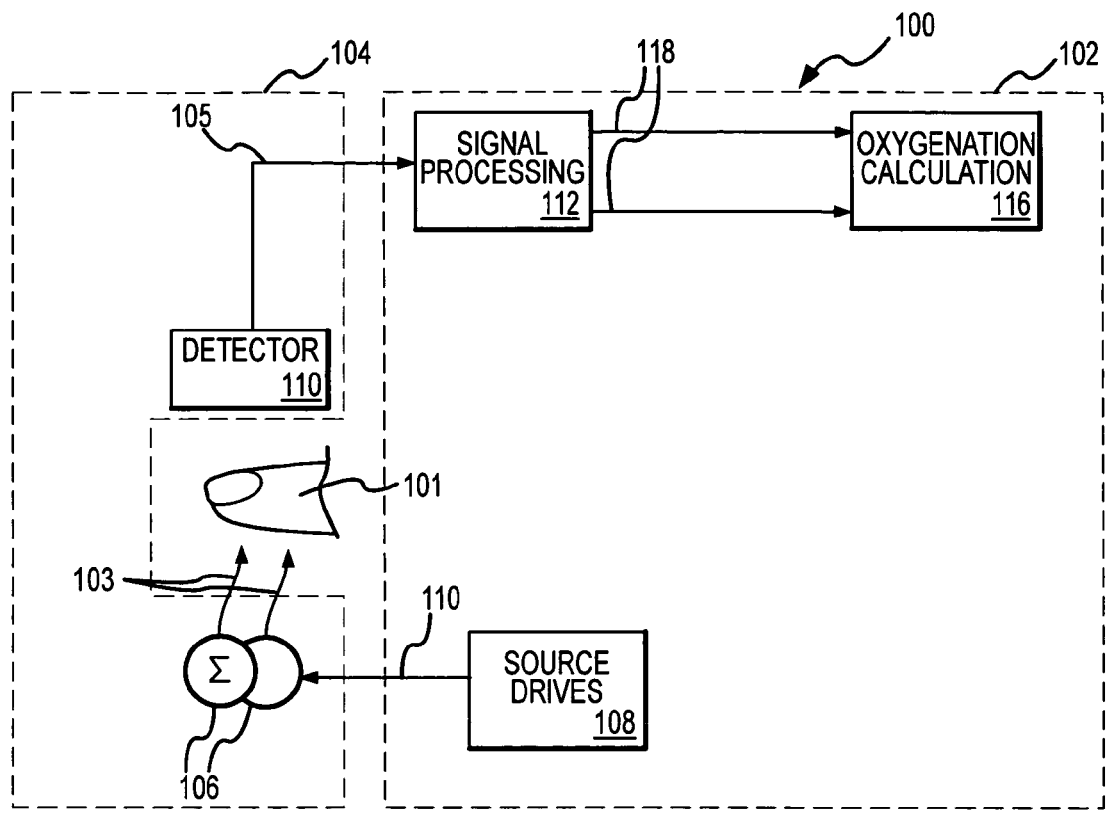
FIG. 1 is a schematic diagram of a pulse oximeter in accordance with the present invention.

The present invention relates to obtaining physiological parameter information for a patient based on an analysis of a pleth signal involving identifying an effect associated with a Mayer Wave component of the pleth signal. In the following discussion, the invention is described in the context of an implementation utilizing components of a conventional pulse oximeter. The invention has particular advantages in this regard as such an implementation enhances the functionality of conventional pulse oximeters and provides important physiological parameter information in a cost effective manner. However, it will be appreciated that various aspects of the invention are not limited to such a pulse oximeter or other multi-channel signal implementations and the invention may be embodied in a dedicated single or multi-channel photoplethysmography instrument. Accordingly, the following discussion should be understood as exemplifying the invention and not by way of limitation.

In accordance with the present invention, physiological parameter information is obtained based on distinguishing an effect associated with the Mayer Wave from an effect associated with the respiration wave. Once such effects are distinguished, the Mayer Wave, the respiration wave or both can be analyzed to obtain the desired information, e.g., regarding the respiratory system, the automatic nervous system or related diagnostics.

The Mayer Wave and the respiration wave can be distinguished in a variety of ways, as will be discussed more fully herein. These include distinguishing based on frequency, based on a wave characteristic other than frequency and based on information not directly derived from Mayer/respiration wave comparison. With regard to the first of these, distinguishing the waves based on frequency can be accomplished in some cases by controlling or having the patient control his respiration rate. An associated methodology and processing system that thereby isolates and analyzes Mayer Wave effects is initially described below. Another aspect of the invention provides a methodology and processing system for analyzing a pleth signal to identify heart rate variability and determine a respiration rate based on that variability. In particular, by isolating the respiration wave (e.g. from a Mayer wave), respiratory sinus arrhythmia and its effects on a patient's heart rate may be monitored. Another aspect of the invention deals with utilizing waveform and/or wave phase to distinguish the Mayer and respiration waves in order to monitor physiological parameters. With regard to the last of the categories noted above, distinguishing the waves based on information not directly derived from Mayer Wave/respiration wave comparison, this can be accomplished by a multi-channel, blood analyte analysis to identify effects related to variations in the ratio of arterial and venous blood in the tissue under consideration associated with the respiratory cycle. Accordingly, associated methodology and processing system that thereby isolates and analyzes respiration wave effects is described below.

Referring to FIG. 1, a schematic diagram of a pulse oximeter 100 in accordance with the present invention is shown. The oximeter 100 generally includes an instrument housing 102 and a probe 104 for attachment to a finger 101 or other appendage of a patient under analysis. In the illustrated embodiment, the probe 104 includes two or more sources 106 and a detector 110. It will be appreciated that either or both of these components may alternatively be located in the housing 102 and may be optically connected to the probe 104 by fiber optics or the like. Additionally, the sources 106 and/or detector 110 may be located in the cable or other coupling operatively between the probe 104 and the housing 102. The sources 106 are driven by source drives 108. The drives 108 serve to modulate the signals 103 in any of various ways. In this regard, the signals 103 transmitted by the sources 106 may be time division multiplexed, frequency division multiplexed, code division multiplexed, or the like. Such multiplexing facilitates separation of the signals from each of the channels during hardware or software based signal processing. The sources 106 provide two or more channels of signals 103. Each channel has a unique spectral content, e.g., wavelength or wavelength band. In the illustrated embodiment, two sources 106 are shown; one of the sources may have a red-centered wavelength and the other may have an infrared-centered wavelength The signals 103 may be transmitted through or reflected by the patient's tissue. In either case, the signals are modulated by the patient's blood to provide information regarding blood oxygen saturation in a manner that is well known. The transmitted signals 103 are received by the detector 110 which, in the illustrated embodiment, provides an analog current output signal 105 representative of the detected signals 103. This detector signal 105 is then processed by signal processing module 112. The processing module 112 may include a number of components that may be embodied in software, firmware and/or hardware. These components may include components for amplifying the signal 105 and converting the signal from a current signal to a voltage signal, filtering the signal to remove certain components of noise and otherwise conditioning the signal. In the illustrated embodiment, the signal processing module 112 also includes an analog to digital converter for converting the signal into a digital signal and a demultiplexer component for providing two separate output signals 118 or pleths that generally correspond to the two separate channel signals 103. These pleths 118 are then used by oxygenation calculation module 116 to compute a value related to blood oxygen saturation, e.g., a blood oxygen saturation percentage. A number of algorithms for performing such calculations are known and such calculation techniques are disclosed in U.S. Pat. No. 5,934,277 by Mortz and U.S. Pat. No. 5,842,979 by Jarman, both of which are incorporated herein by reference.

The present aspect of the invention involves monitoring effects related to the Mayer Wave such as low frequency blood volume and heart rate variability. An implementation for monitoring heart rate variability is discussed below followed by an implementation for monitoring blood volume variability. Both cases involve analysis of a pleth signal.

Figure 2:
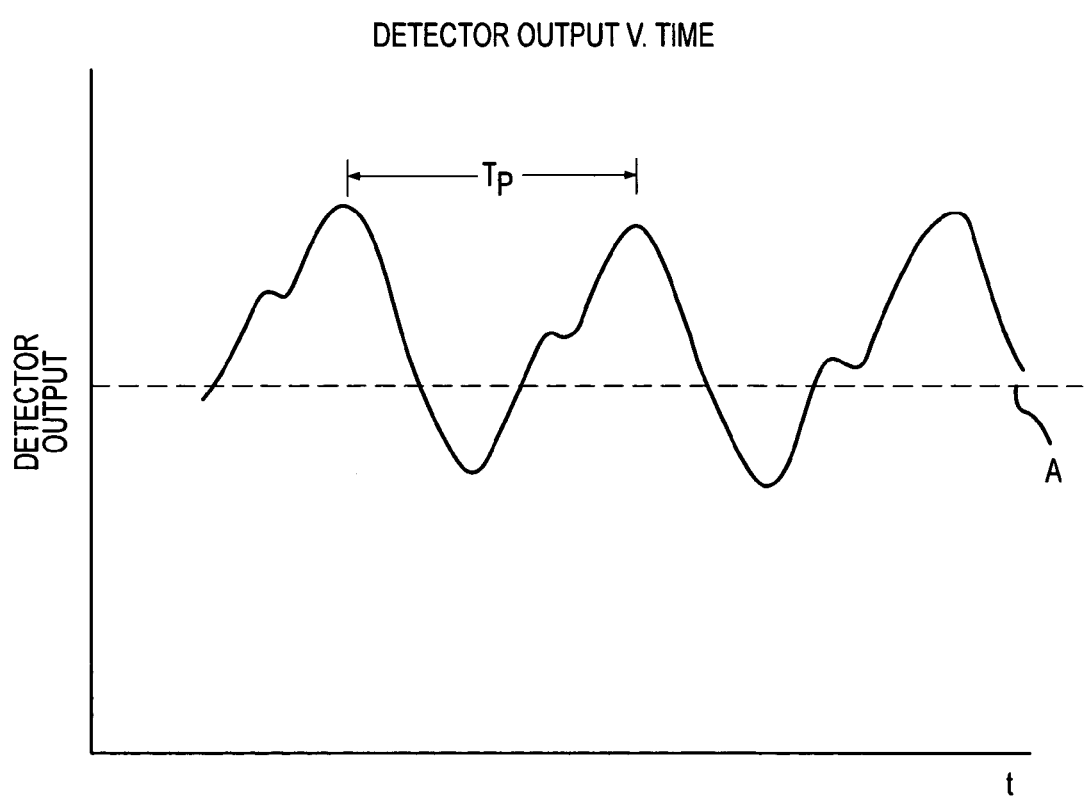
FIG. 2 illustrates the waveform of a pleth that may be used to obtain physiological parameter information in accordance with the present invention.

FIG. 2 illustrates an exemplary waveform of a pleth as such information may be obtained by the processor of a pulse oximeter. In particular, such information may be obtained as a digital signal output by the A/D converter, i.e., a time series of values related to the detector output. Such values are shown graphically in FIG. 2. As noted above, the pleth corresponding to either of the oximetry channels, or a combination of the channels, may be used in accordance with the present invention. It is desirable to obtain a strong pleth signal so that the waveform and pulse rate can be accurately identified. Accordingly, for normally oxygenated patients, the infrared channel pleth may be utilized. For poorly oxygenated patients, the red pleth may be preferred. In this regard, a cut off oxygenation level such as 85% may be used in determining whether to use the infrared or red pleth. Alternatively, the two pleth signals may be mathematically blended, depending on the current oxygenation level to obtain an optimized pleth for subsequent analysis in accordance with the present invention. Such selection or blending of the individual channel pleth signals is described in detail in U.S. patent application Ser. No. 09/975,289 by Hanna, which is incorporated herein by reference.

As shown in FIG. 2, the pleth signal includes a pulsatile component having a period designated $T_p$. This period corresponds to the patient's heart rate. The heart rate can be determined by monitoring this pleth in a variety of ways such as identifying a change in sign of a differential value of the waveform, tracking crossings of an average value indicated by A, or, as will be discussed in more detail below, by using a filter to track the fundamental frequency of the pleth.

Figure 3:
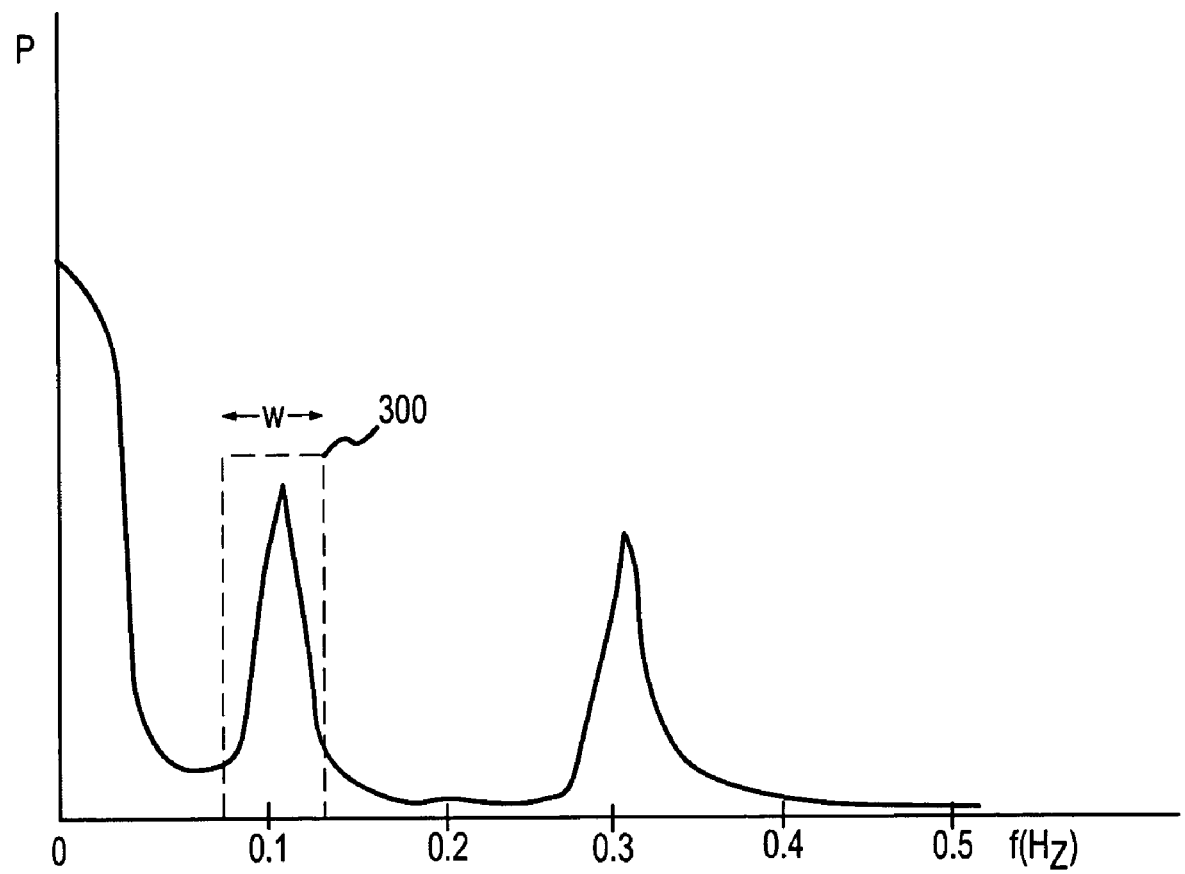
FIG. 3 is a graph illustrating the low frequency power spectrum of a pleth signal and a pass band of a filter used in accordance with the present invention.

In accordance with the present invention, the patient's respiration is monitored by tracking low frequency heart rate changes. FIG. 3 shows an exemplary pleth power spectrum. The spectrum is characterized by three discrete peaks. These include a peak typically around 0.3–0.5 Hz, a peak typically around 0.1 Hz and a peak below 0.05 Hz. The peak below 0.05 Hz is generally linked with vaso motor control and temperature control. The peak at around 0.1 Hz is generally associated with the Mayer Wave. As noted above, this phenomenon is not well understood but has been correlated to hypertension, sudden cardiac death, ventricular tachycardia, coronary artery disease, myocardial infarction, heart failure, diabetes, and autonomic neuropathy and,has been seen to change after heart transplantation. The remaining peak, at about 0.3–0.5 Hz is believed to be correlated with respiration. This peak may have a significantly higher frequency for infants.

From the foregoing discussion, it will be appreciated that low frequency heart rate variability associated with the Mayer Wave can be monitored by: 1) determining heart rate based on an analysis of the pleth signal, 2) monitoring this heart rate over time to obtain a time series heart rate values, and 3) analyzing the time series heart rate values to identify a low frequency variability. These steps can be executed using adaptive filters as discussed below.

Figure 4:
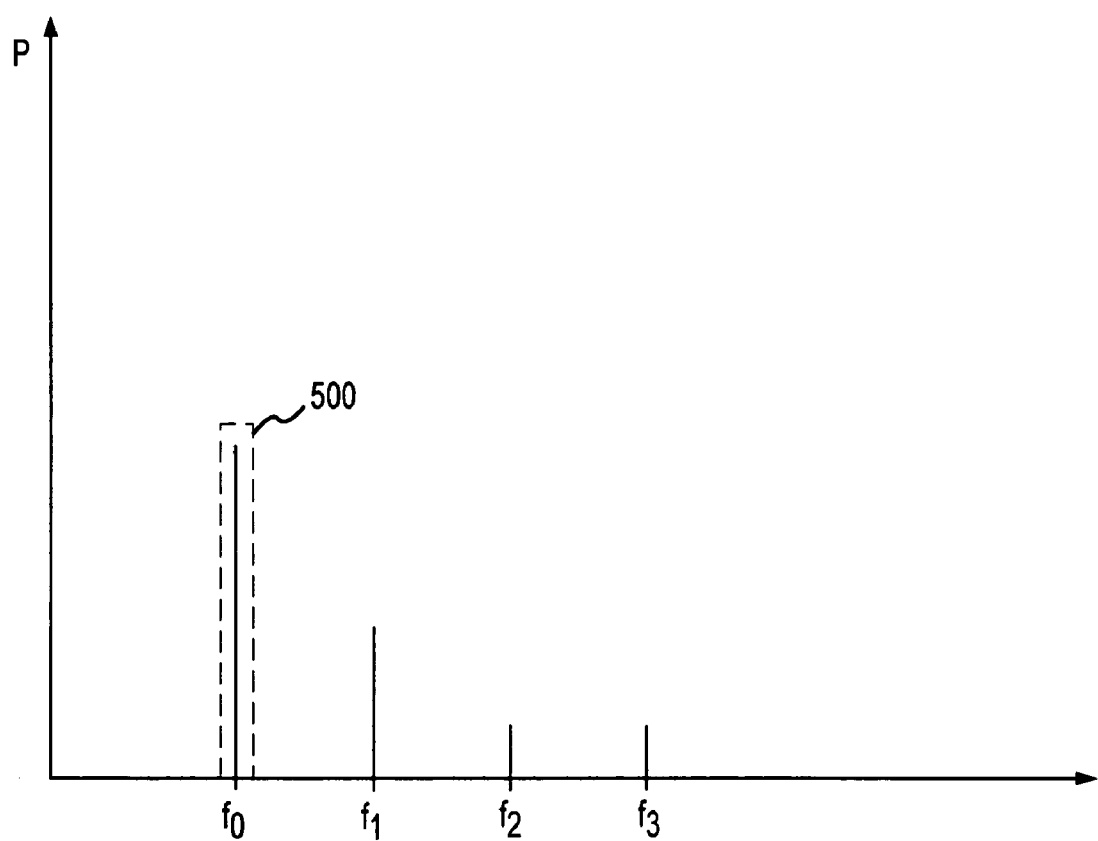
FIG. 4 is a chart illustrating a pleth signal power spectrum and a pass band of a filter used in accordance with the present invention.

FIG. 4 illustrates a pleth power spectrum. Such a power spectrum may be obtained by configuring the oximeter processor to mathematically obtain a Fourier transform of the time domain pleth signal. As shown, the pleth power spectrum has a fundamental frequency at $t_0$ corresponding to the patient's heart rate. Additional peaks of the illustrated power spectrum relate to harmonics thereof. The present invention utilizes an adaptive filter adapted to function as a band pass filter having a narrow band pass encompassing the fundamental frequency. The transfer function of this filter is generally indicated by function 500. A variety of different types of filters may be used in this regard. Generally, such filters track the fundamental frequency of a signal based on certain programmed information regarding the nature of the signal as well as by monitoring successive signal waveforms. Such filters are robust in operation and can provide a continually updated output, in this case, regarding pulse rate. Thus, such a filter can provide as an output a time series of pulse rates of values or pulse rate signal.

An additional digital filter can be used to extract from this pulse rate signal a low frequency variation therein associated with the Mayer Wave. Referring again to FIG. 3, the Mayer Wave has a frequency around 0.1 Hz. Accordingly, the low frequency variation in pulse rate associated with the Mayer Wave can be extracted from the pulse rate signal by filtering the pulse rate signal using a band pass filter having a pass band encompassing the Mayer Wave frequency. The transfer function of such a band pass filter is graphically illustrated by function 300 of FIG. 3. This band pass has a width, w, and a center frequency selected to pass the Mayer Wave components and substantially exclude interference from the very low frequency peak and the peak associated with the respiration wave as discussed above. On the other hand, the width, w, should be sufficient to accommodate small variations in Mayer Wave frequency which are of interest for diagnostic purposes. Accordingly, the lower end of the pass band is preferably at least 0.05 Hz. As noted above, the upper end of the pass band can be selected in conjunction with the patient's respiration rate which may be controlled. Thus, the upper end of the pass band is preferably no greater than about 0.5 Hz or 1.5 Hz to accommodate neonatal applications and, more preferably, is no greater than about 0.3 Hz. In the illustrated embodiment, the band pass filter has a lower limit of about 0.08 Hz and an upper limit of about 0.4 Hz. Alternatively, an adaptive filter may be Used to track the Mayer Wave component. In particular, such an adaptive filter may function as a band pass filter having a transfer function that can shift to track the frequency of the Mayer Wave component.

Figure 5:
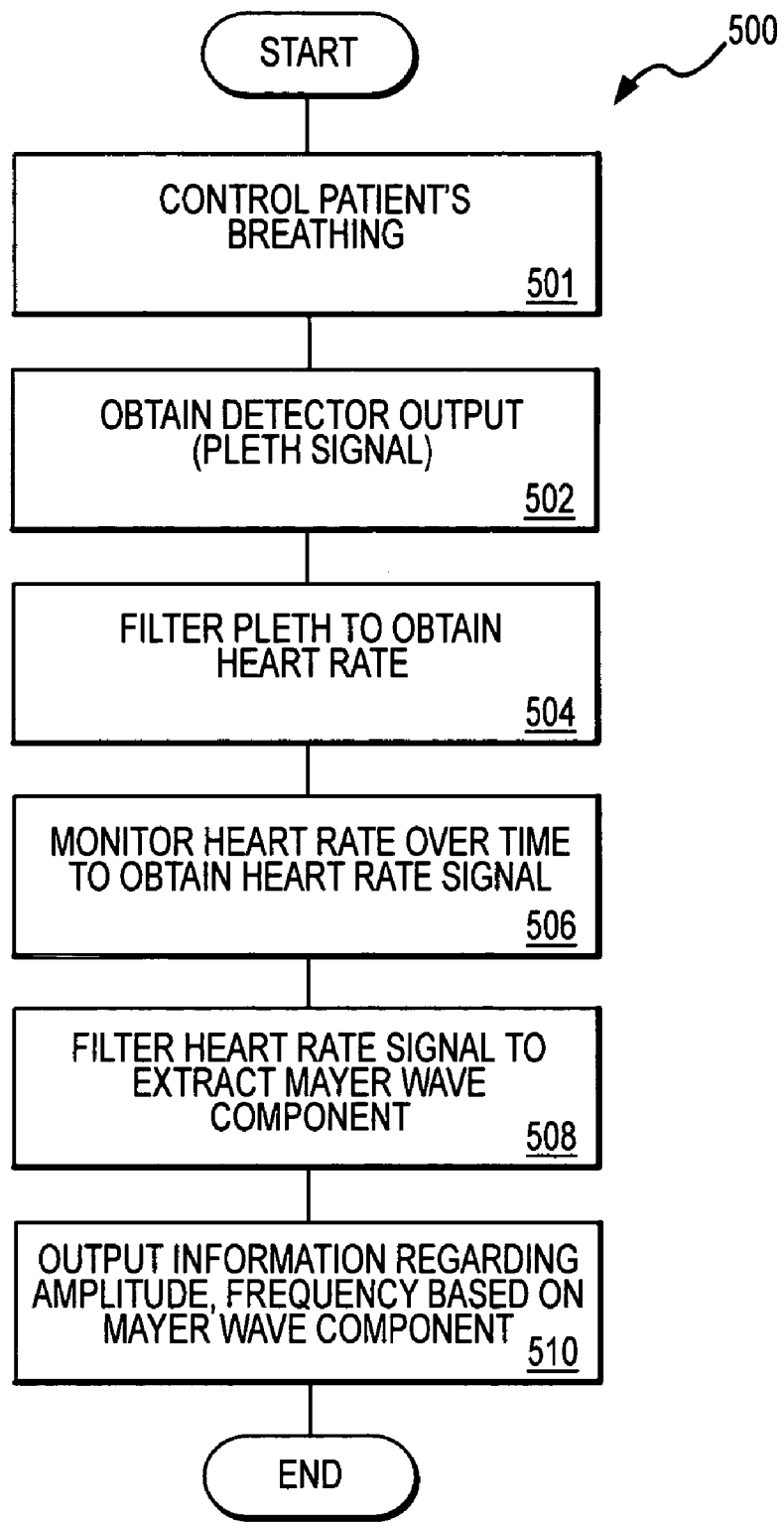
FIG. 5 is a flow chart illustrating a process for monitoring a Mayer Wave effect based on a photoplethysmographic heart rate signal in accordance with the present invention.

FIG. 5 is a flow chart illustrating a process for monitoring low frequency variations in heart rate based on pleth signals in accordance with the present invention. The process 500 is initiated by controlling (501) the patient's breathing to be at a frequency of at least a predetermined threshold and obtaining (502) a detector output or pleth signal. The patient's breathing may be controlled by instructing the patient to breath at the desired rate or by using a respirator. The threshold may be selected based on the pass band of the filter as discussed above. In the context of a pulse oximeter, obtaining the pleth signal may involve receiving the digital output from an A/D converter that reflects the detector signal, demodulating this signal to obtain individual channel components and selecting a pleth for further processing. The selected pleth may be one of the channels or an optimized pleth signal based on both of the channel components. The pleth is then filtered (504), e.g., using an adaptive filter to track the fundamental frequency of the pleth signal, to obtain a time series of heart rate values. These values are monitored (506) over time to obtain a heart rate signal. The heart rate signal is then filtered (508) using a band pass filter or adaptive filter as discussed above to extract a frequency component related to the Mayer Wave. Information regarding this frequency component is then output (510), e.g., as a graphical waveform display or as numerical values. Preferably, this information relates to an amplitude, frequency or variation therein based on the extracted Mayer Wave component. This information may be displayed in the display area of a conventional pulse oximeter programmed to provide such information.

Figure 6:
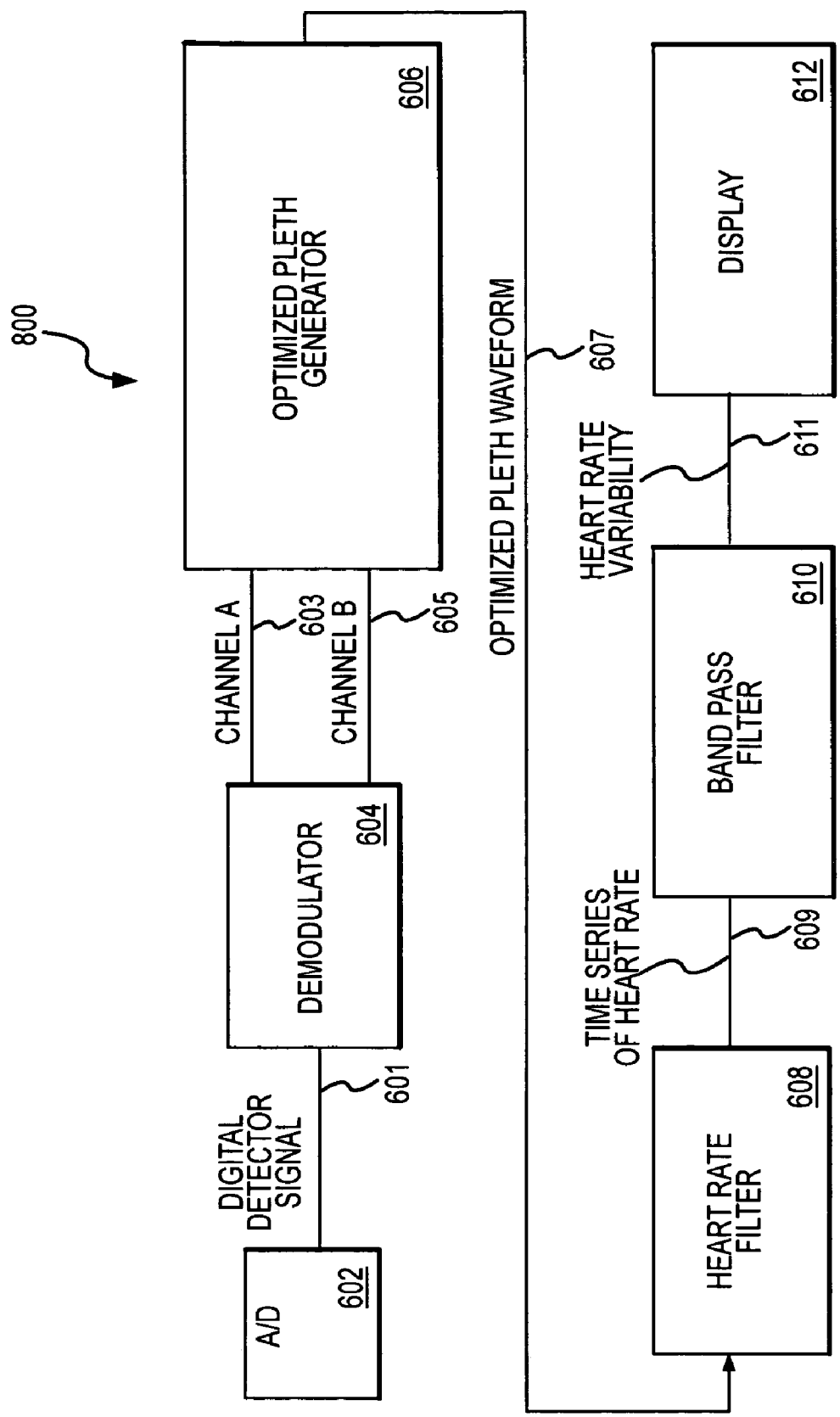
FIG. 6 is a schematic diagram of a pulse oximetry system adapted for monitoring a Mayer Wave effect based on a photoplethysmographic heart rate signal.

The corresponding components of a pulse oximeter processing unit are illustrated in FIG. 6. The illustrative unit 600 includes an A/D converter 602. The A/D converter 602 receives an analog signal representative of the optical signal received by the pulse oximeter detector. This analog input signal is processed by the converter (602) to provide a digital detector signal 603. The digital detector signal 603 is then processed by demodulator 604 to provide two separate channel signals designated channel A (605) and channel B (607), that may correspond, for example, to the red and infrared channels of the pulse oximeter. These channel signals are then processed in the illustrated embodiment by the optimized pleth generator 606 to provide an optimized pleth waveform 609. As discussed above, the optimized pleth waveform may correspond to either of the channel signals or a combination thereof. This optimized waveform 609 is processed by a heart rate filter in order to track the fundamental frequency of the waveform which corresponds to the patient's heart rate. The output from the heart rate filter 608 is a time series of heart rate values 611. This time series heart rate values is then processed by a band pass filter 610 which passes the Mayer Wave component of the corresponding spectrum to identify the associated low frequency heart rate variability. Associated information 613 may be periodically output to a user via a display 612.

FIGS. 7–17 relate to monitoring an alternative Mayer Wave effect; namely, low frequency blood volume variability. As noted above, the Mayer Wave is associated with a number of effects including low frequency variability in heart rate, blood volume, blood pressure and vasoconstriction. It will be appreciated that variations in blood volume can be directly monitored from the pleth signal. In particular, the attenuation of optical signals in a pulse oximeter is proportional to the effective optical path length which in turn is related to blood volume. A number of factors affect blood volume including, notably, the patient's pulse. Thus, the pleth signal will include a component having a pulsatile waveform. This pulsatile waveform is effectively modulated by the Mayer Wave. Thus, if potentially interfering effects such as patient respiration are accounted for, the Mayer Wave component be extracted from the pleth signal by band pass filtering using a band pass filter or adaptive filter as discussed above in connection with FIG. 3 (in this case used to filter the pleth signal rather than a heart rate signal). The patient's breathing can be controlled to have a frequency outside of the pass band of this filter. In particular, when possible, the patient can be instructed to breathe at a frequency of at least 0.167 Hz (10 breaths per minute) and, more preferably, at least about 0.333 Hz (20 breaths per minute). Alternatively, the patient's breathing can be controlled in this regard using a respirator.

Figure 7:
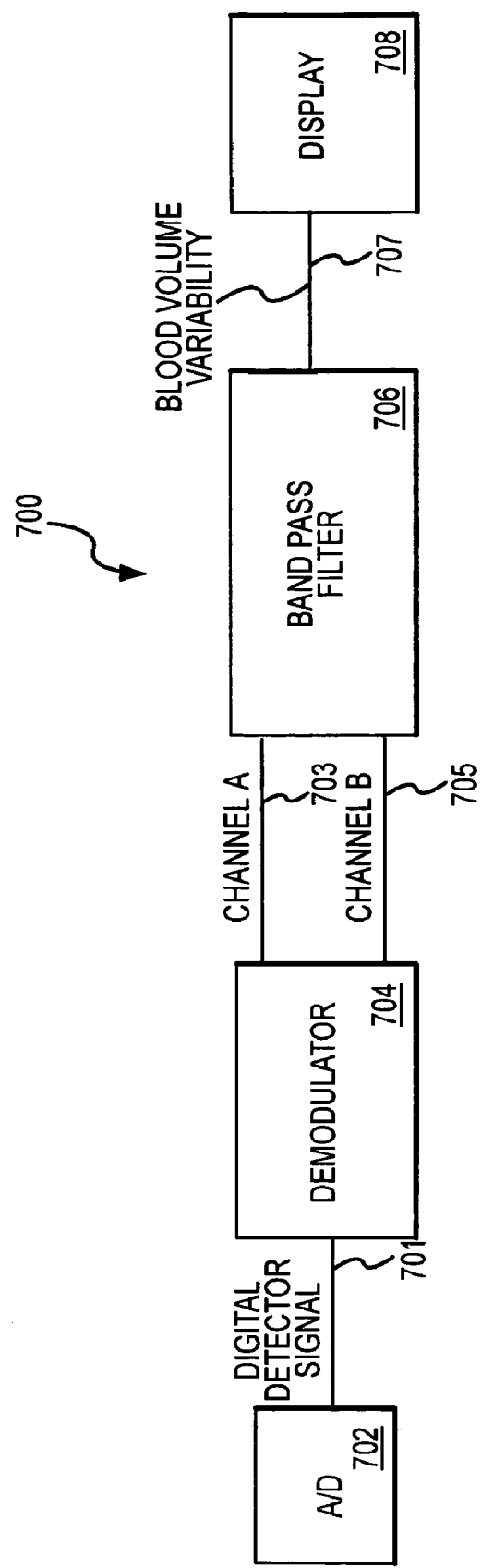
FIG. 7 is a schematic diagram of a pulse oximetry system adapted for monitoring low frequency blood volume variability in accordance with the present invention.

The corresponding components of a pulse oximeter processing unit are illustrated in FIG. 7. The illustrated unit 700 includes and A/D converter 702. The A/D converter functions as described above in connection with FIG. 6 to receive an analog signal representative of the optical signal received by the pulse oximeter detector and provide a corresponding digital detector signal 701. The digital detector signal 701 is then processed by a demodulator 704 to provide two separate channel signals designated channel A (703) and channel B (705), that may correspond, for example, to the red and infrared channels of the pulse oximeter. The pleth signal corresponding to either one of these channels or a combined signal based on both channels is then filtered by band pass filter 706 as described above to extract a component 707 related to blood volume variability. Information related to blood volume variability is then provided via the display 708. Such information may include a waveform of the blood volume variability signal, a frequency or amplitude of the blood volume variability waveform and/or a value related to a variation of the amplitude or frequency.

Figure 8:
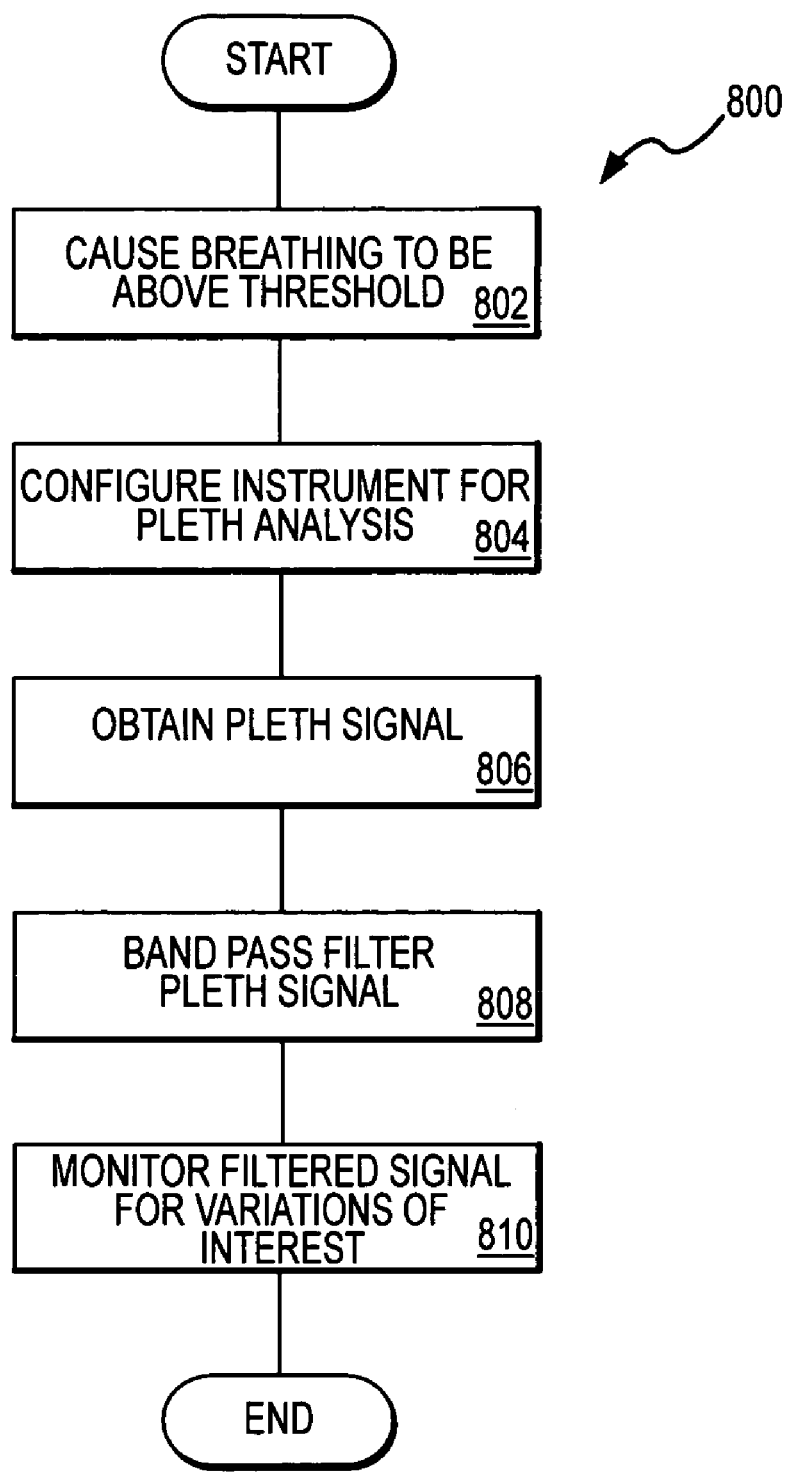
FIG. 8 is a flow chart illustrating a process for monitoring low frequency blood volume variability in accordance with the present invention.

FIG. 8 is a flow chart illustrating a process 800 for monitoring blood volume variability. The process 800 is initiated by causing (802) a patient's breathing rate to be above a selected threshold. As discussed above, when possible, the patient may be instructed to control his breathing. Alternatively, the patient's breathing may be artificially controlled. For example, the patient's breathing rate may be controlled to be at least about 10 breaths per minute and more preferably at least about 20 breaths per minute. The pulse oximetry instrument is then configured (804) to obtain a pleth signal, e.g., by placing a probe on the patient's finger, and the instrument is operated to obtain (806) a pleth signal. This pleth signal, which may correspond to one or more of the oximeter channels, is then band pass filtered (808) to extract a low frequency blood volume variability component associated with the Mayer Wave. The filtered signals are monitored (810) to identify any variations of interest. In this regard, variations in the amplitude or frequency of the Mayer Wave may be of diagnostic significance.

Figure 9:
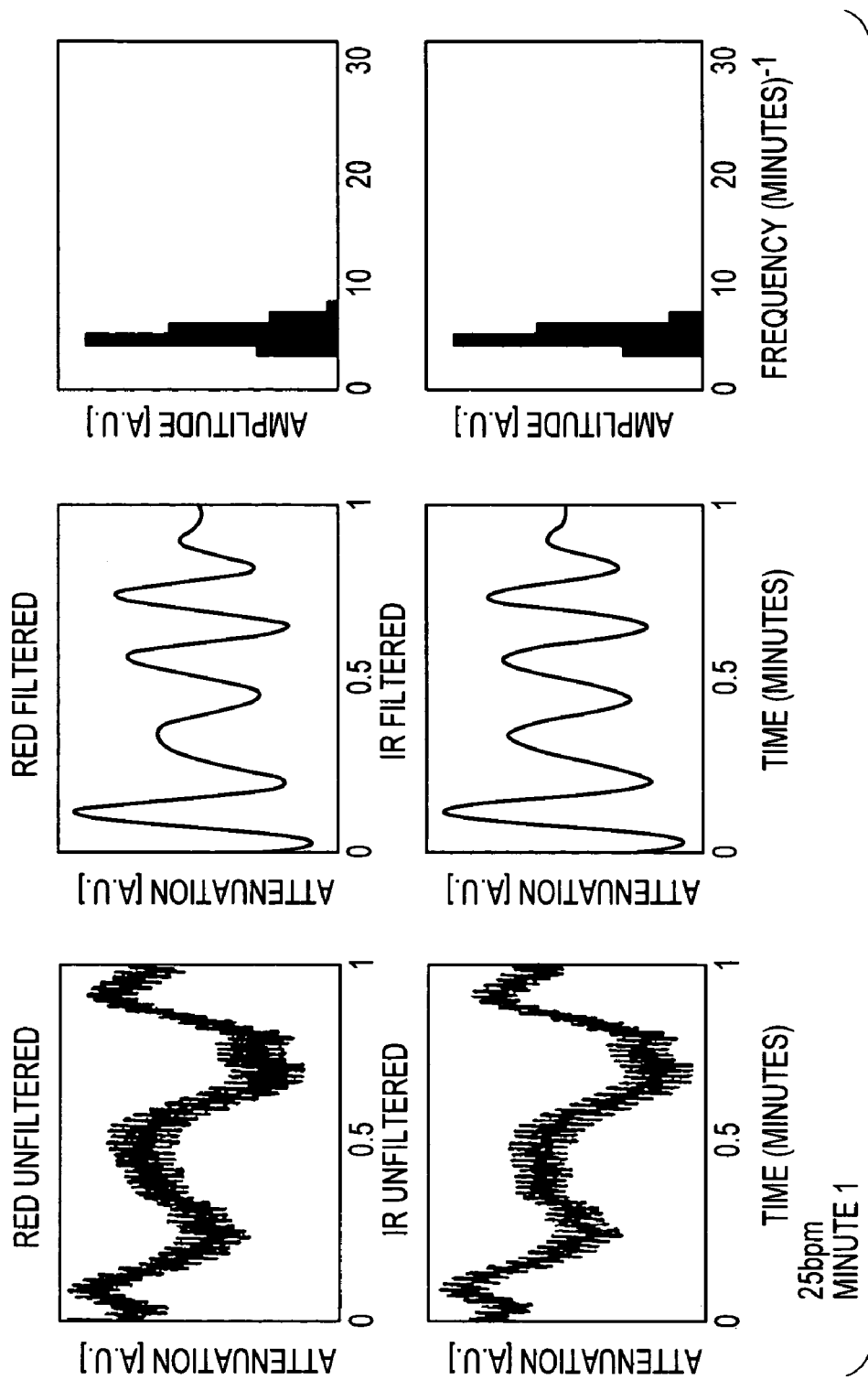
FIGS. 9–16 illustrate the results of various procedures performed to monitor Mayer Wave effects in accordance with the present invention.
Figure 10:
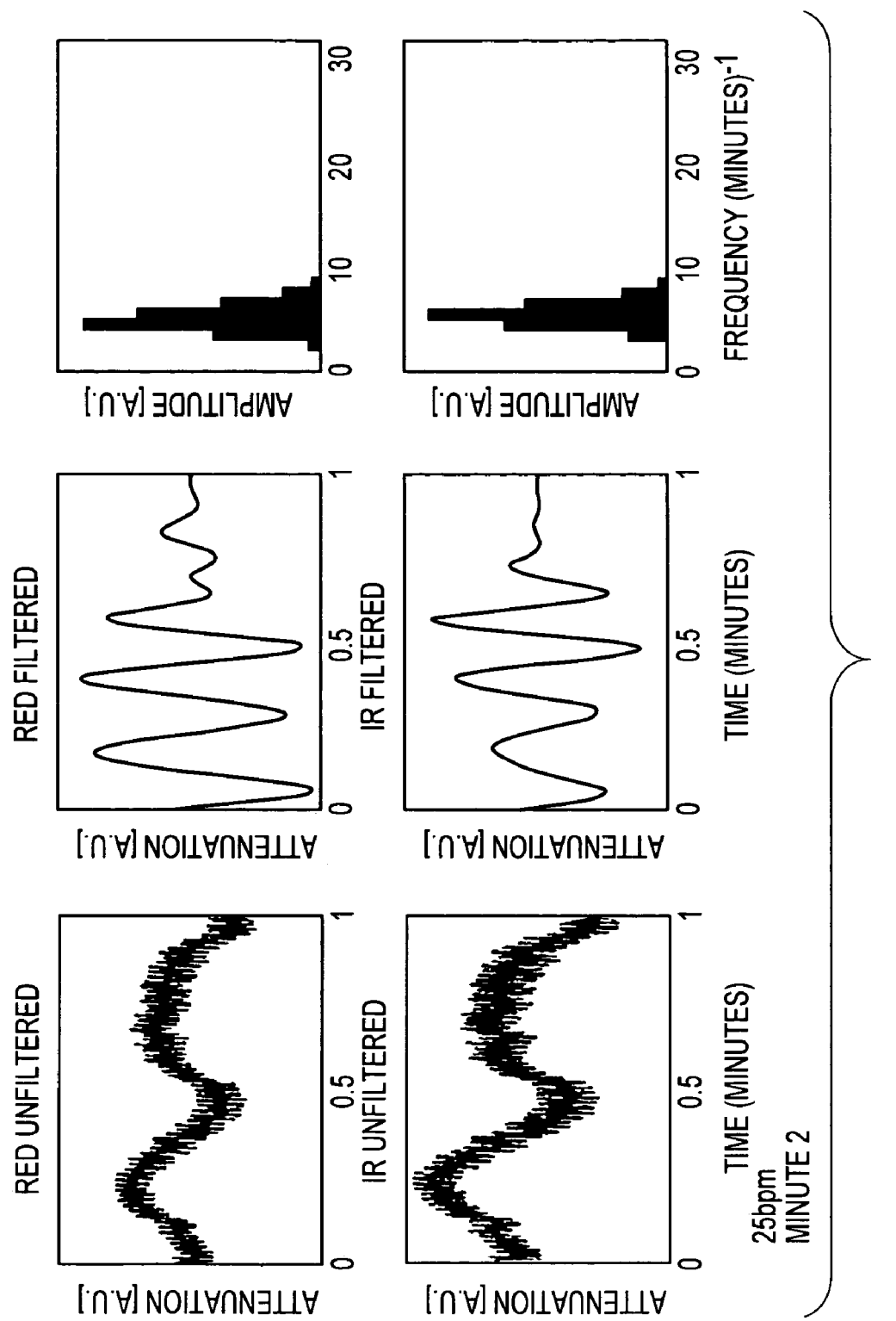
Figure 11:
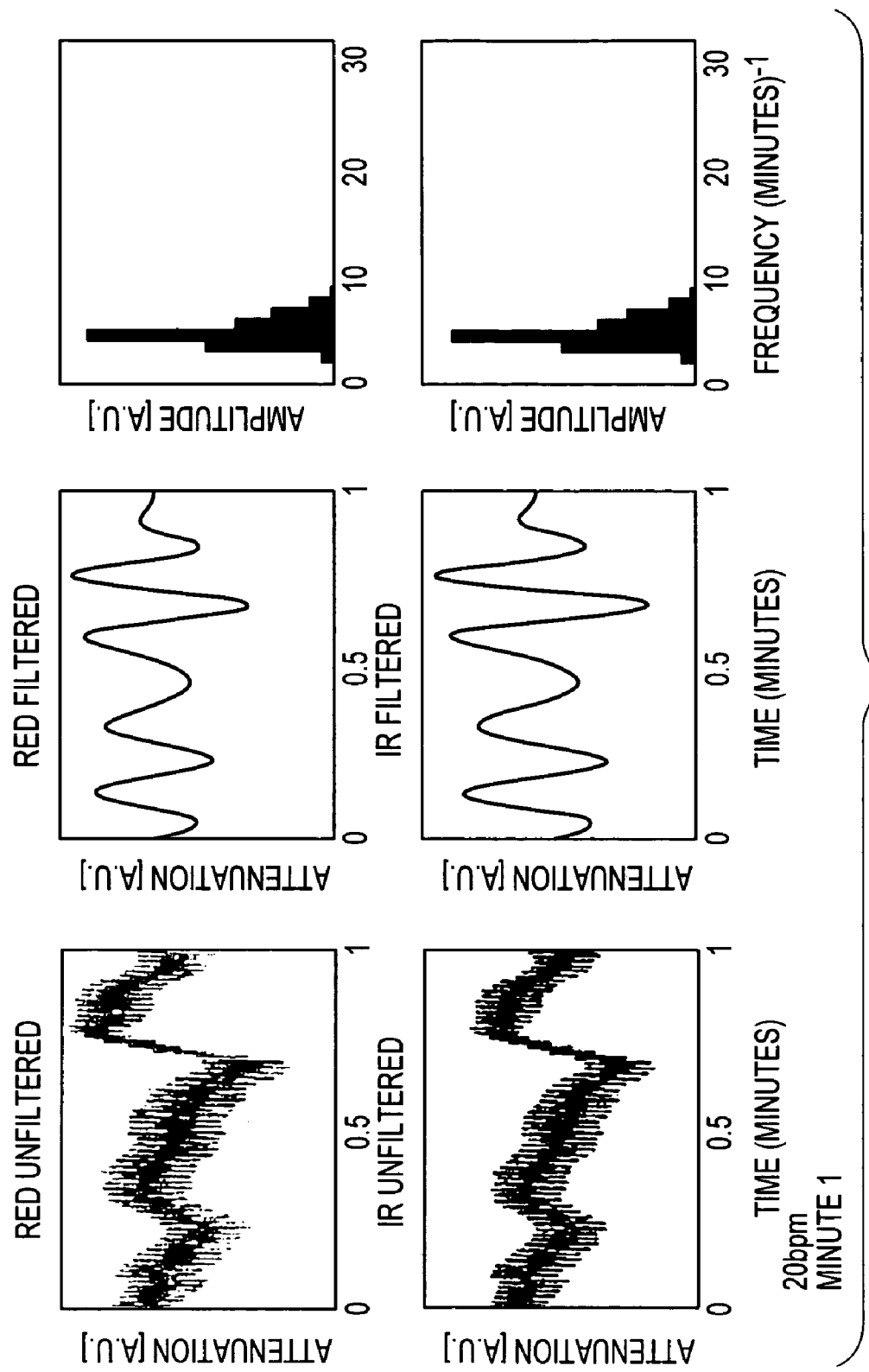
Figure 12:
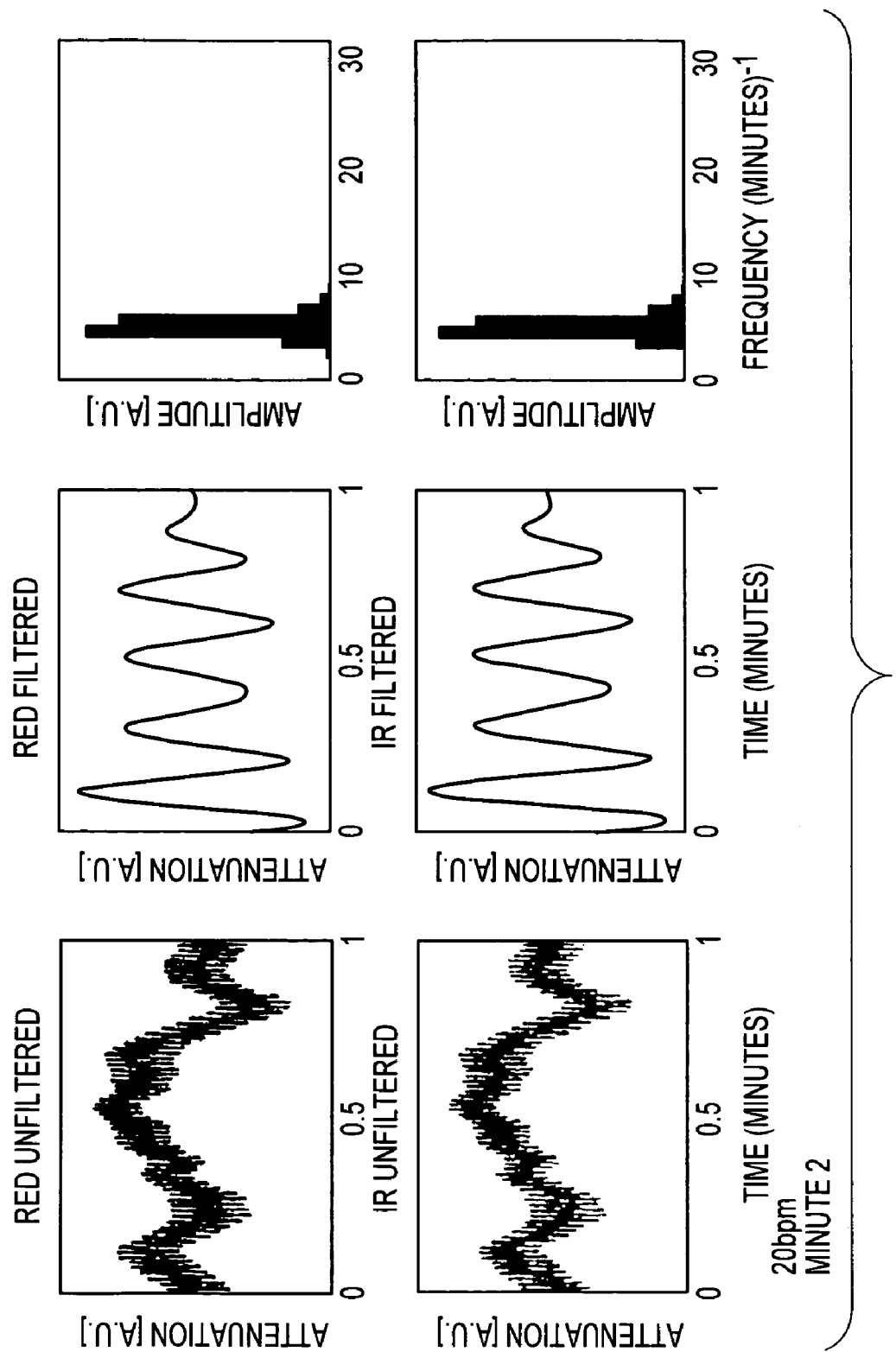
Figure 13:
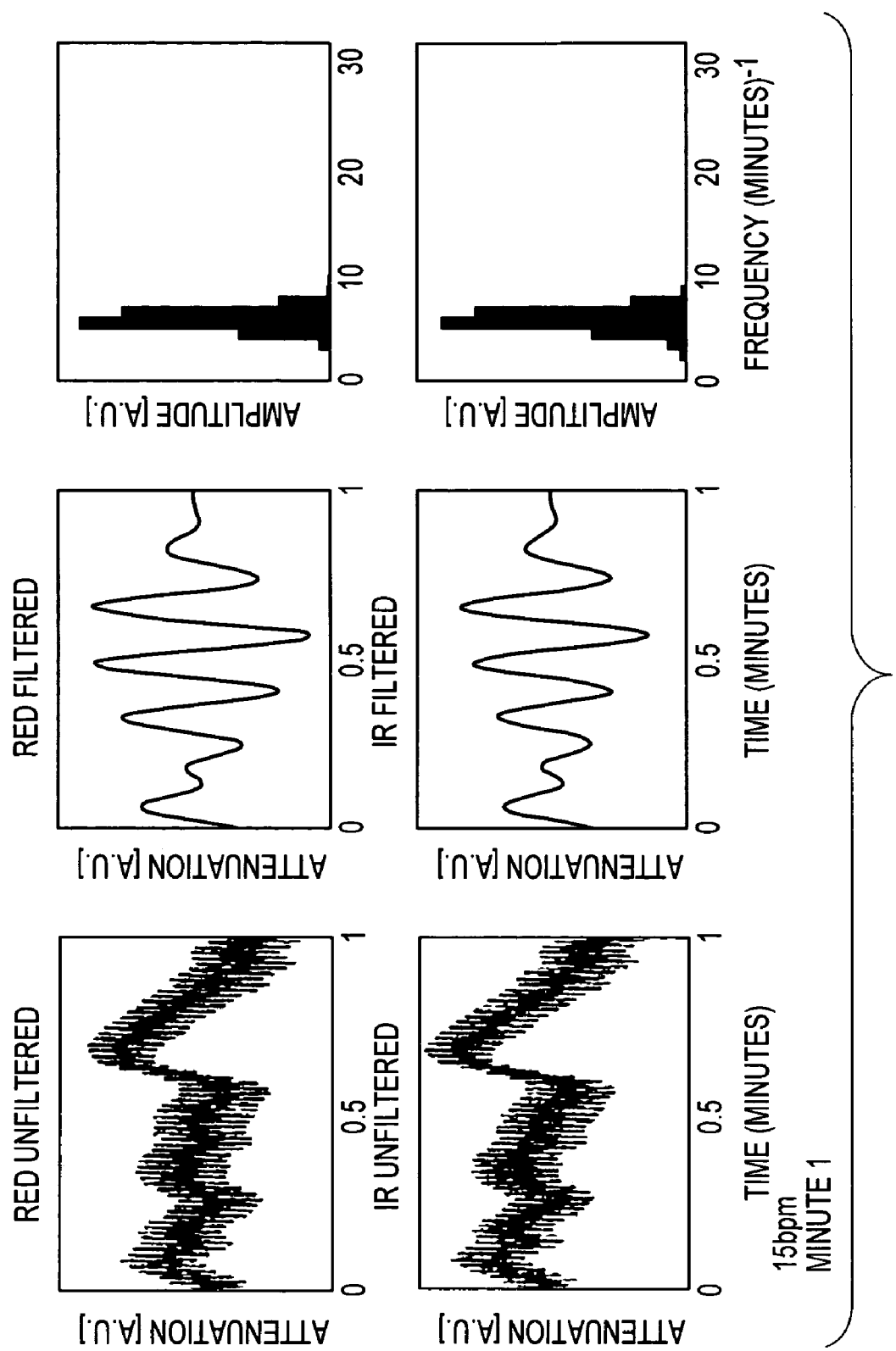
Figure 14:
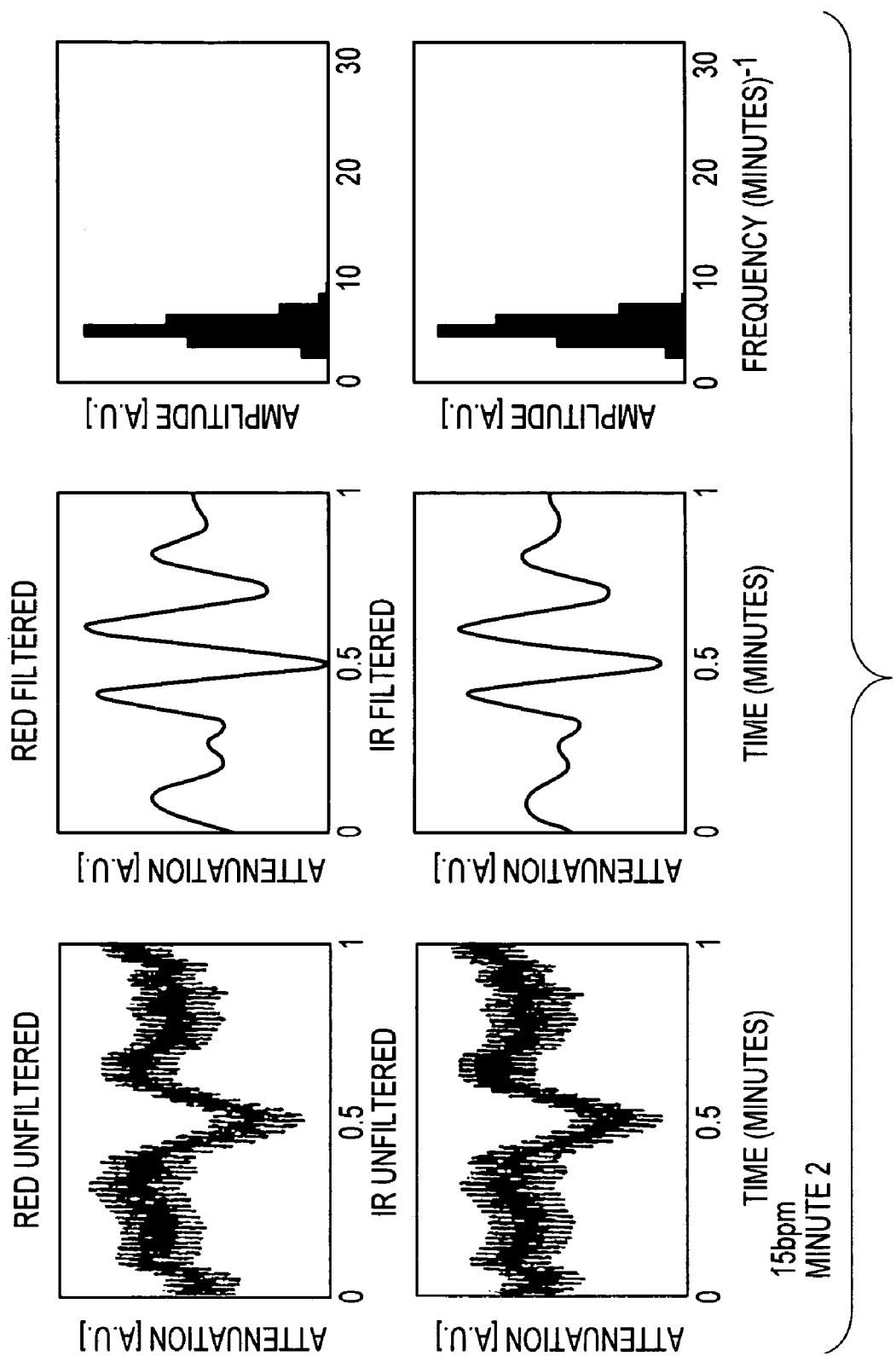
Figure 15:
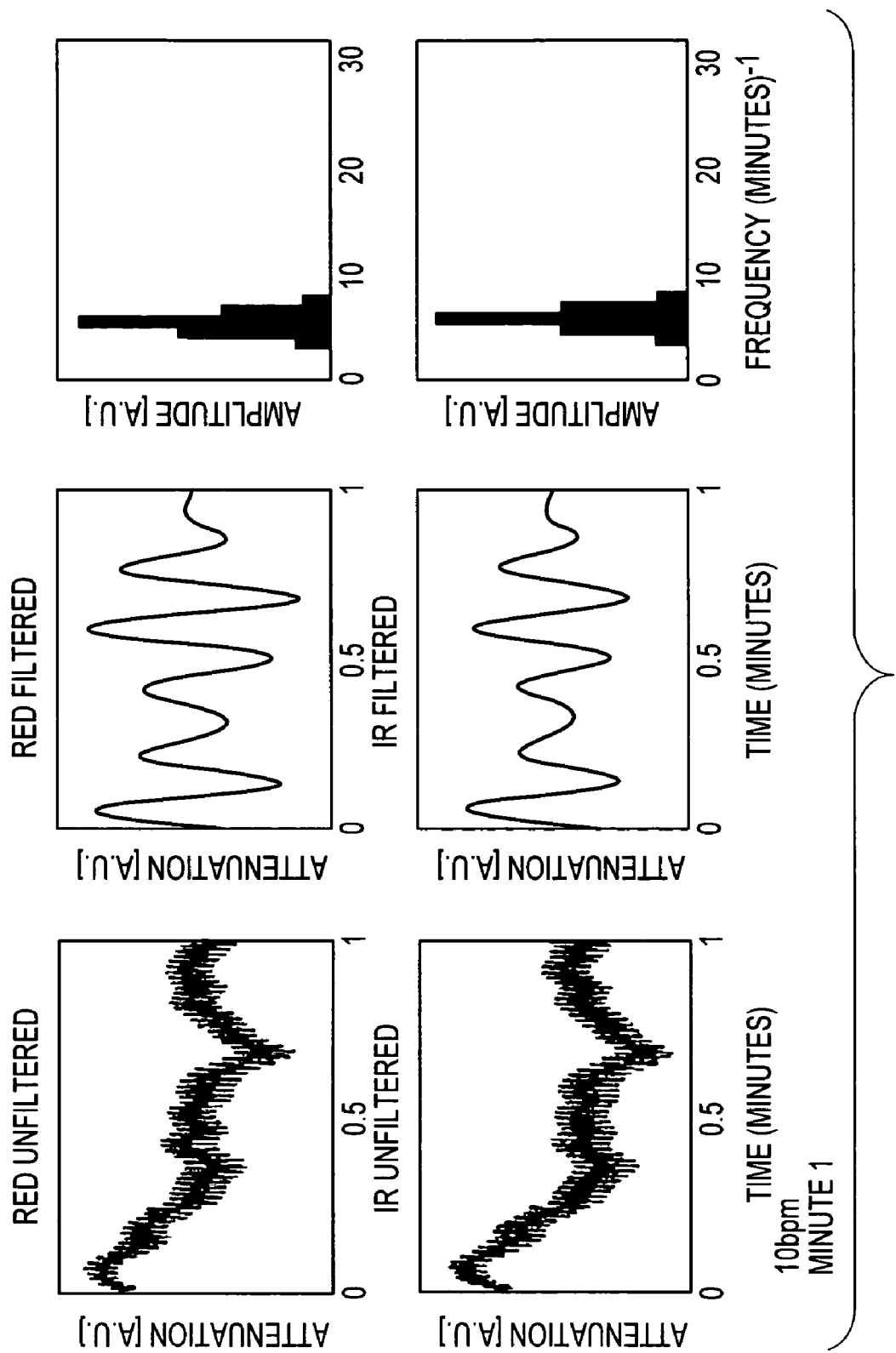
Figure 16:
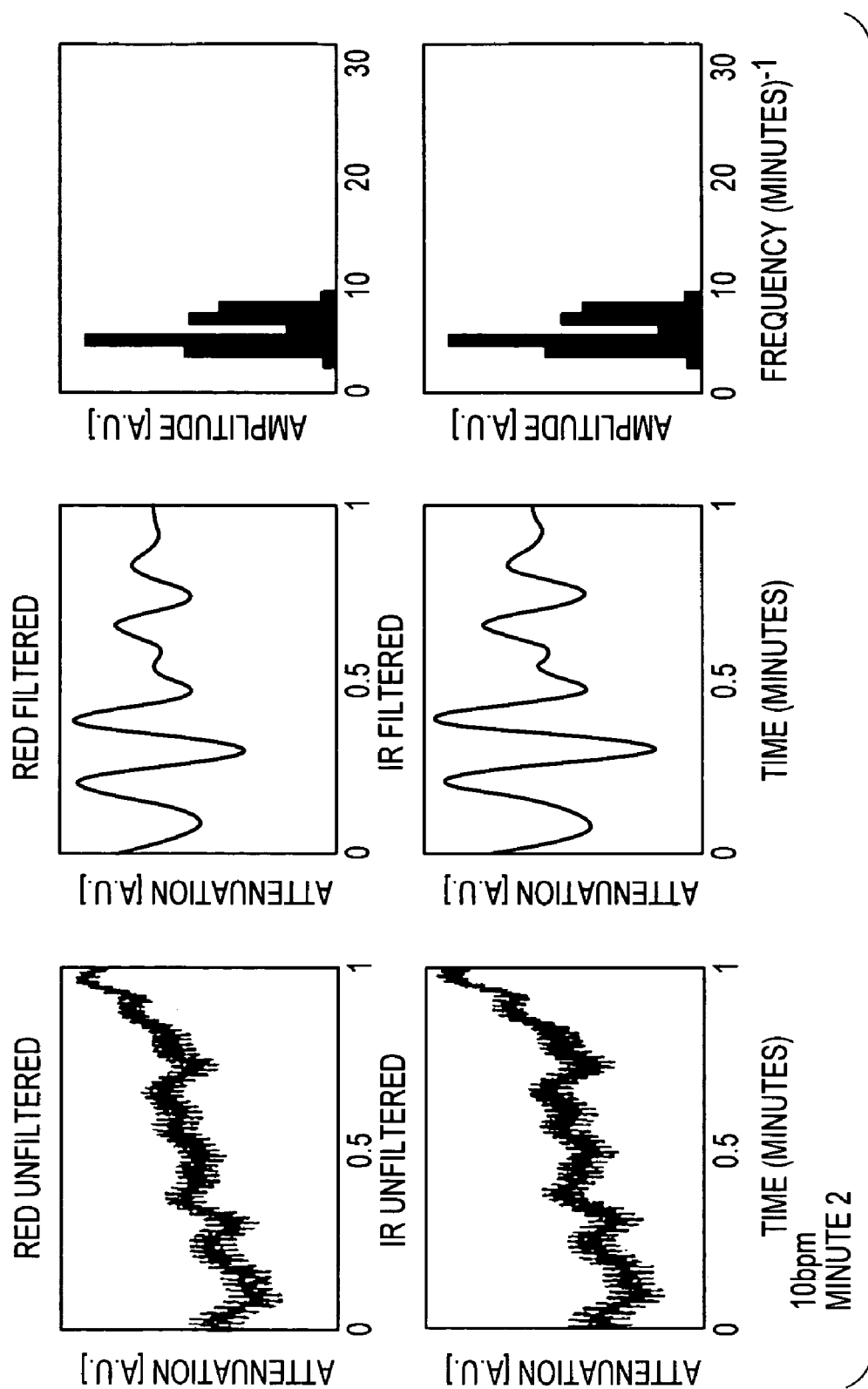

FIGS. 9–16 illustrate the results of procedures performed in accordance with the present invention. In particular, four two minute measurements were conducted on a subject breathing at 25, 20, 15 and 10 breaths per minute. FIG. 9 illustrates the results for the first minute at 25 breaths per minute, FIG. 10 shows the results for the second minute at a breathing rate of 25 breaths per minute, FIG. 11 shows the results for the first minute at 20 breaths per minute, FIG. 12 shows the results for the second minute at 20 breaths per minute, FIG. 13 shows the results for the first minute at 15 breaths per minute, FIG. 14 shows the results for the second minute at 15 breaths per minute, FIG. 15 shows the results for the first minute at 10 breaths per minute and FIG. 16 shows the results for the second minute at 10 breaths per minute. Each of these Figures includes top and bottom rows of panels corresponding to the red and infrared channels, respectively, of the pulse oximeter detector signal. Each row includes a first panel that shows the unfiltered pleth signal, a second panel that shows the pleth signal after filtering to extract the Mayer Wave related component of blood volume variability and the final panel shows the resulting spectrum of the low frequency blood volume variability related to the Mayer Wave. As shown, the amplitude and frequency of the Mayer Wave related components are clearly visible in each of the test results, thus allowing for monitoring of a Mayer Wave effect of potential diagnostic significance.

Figure 17:
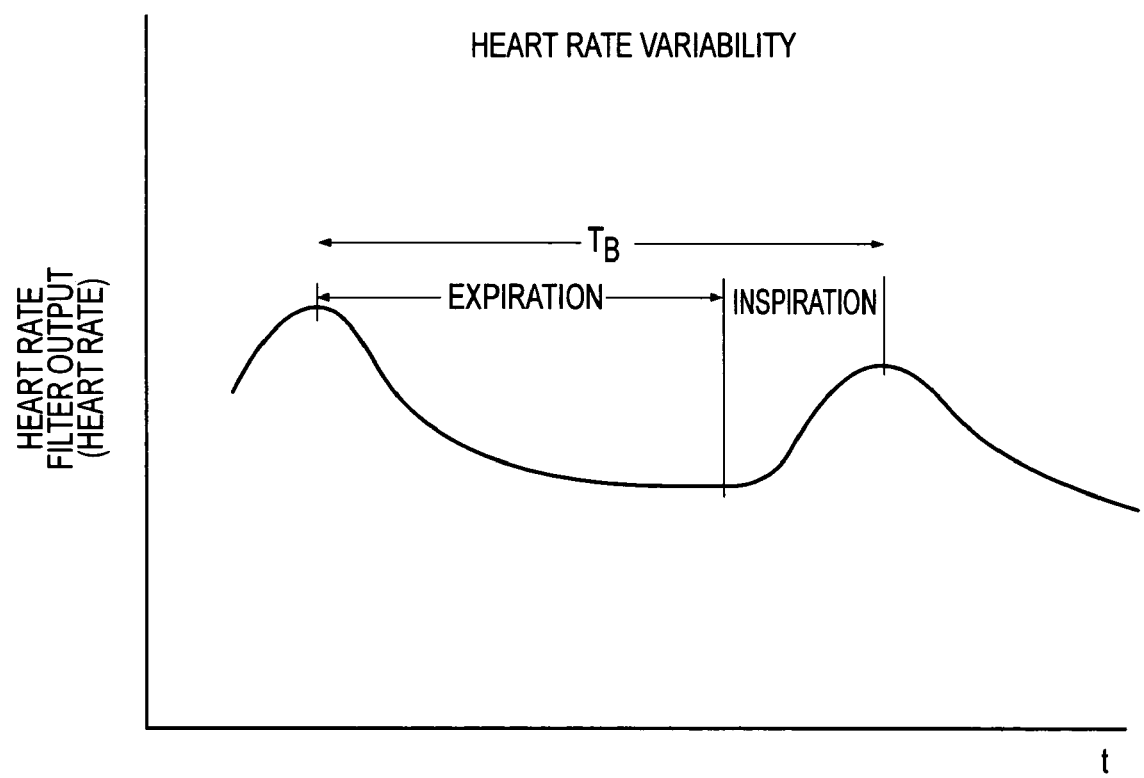
FIG. 17 illustrates a heart rate time series generated using an appropriate filter in accordance with the present invention.

In another implementation of the present invention, a pleth signal is analyzed to identify a heart rate variability parameter associated with respiration rate. In this regard, FIG. 17 graphically illustrates the respiratory Sinus Arrhythmia phenomenon associated with the respiration wave discussed in conjunction with FIG. 3. In particular, FIG. 17 is a graph plotting the output of a heart rate filter, as will be discussed below, against time. As shown, the result is a periodic waveform having a period designated $T_B$. This generally corresponds to a reduction in heart rate during the expiration portion of the respiratory cycle and an increase in heart rate during the inspiration portion of the cycle. The period of this waveform generally corresponds to the respiration rate and is tracked using a pulse oximeter in accordance with the present invention.

From the foregoing discussion, it will be appreciated that respiration rate can be monitored by: 1) determining heart rate based on an analysis of the pleth signal, 2) monitoring this heart rate over time to obtain a time series heart rate values, and 3) analyzing the time series heart rate values to identify a respiration rate. These steps can be executed using adaptive filters and/or static band pass filters as discussed below.

Figure 18:
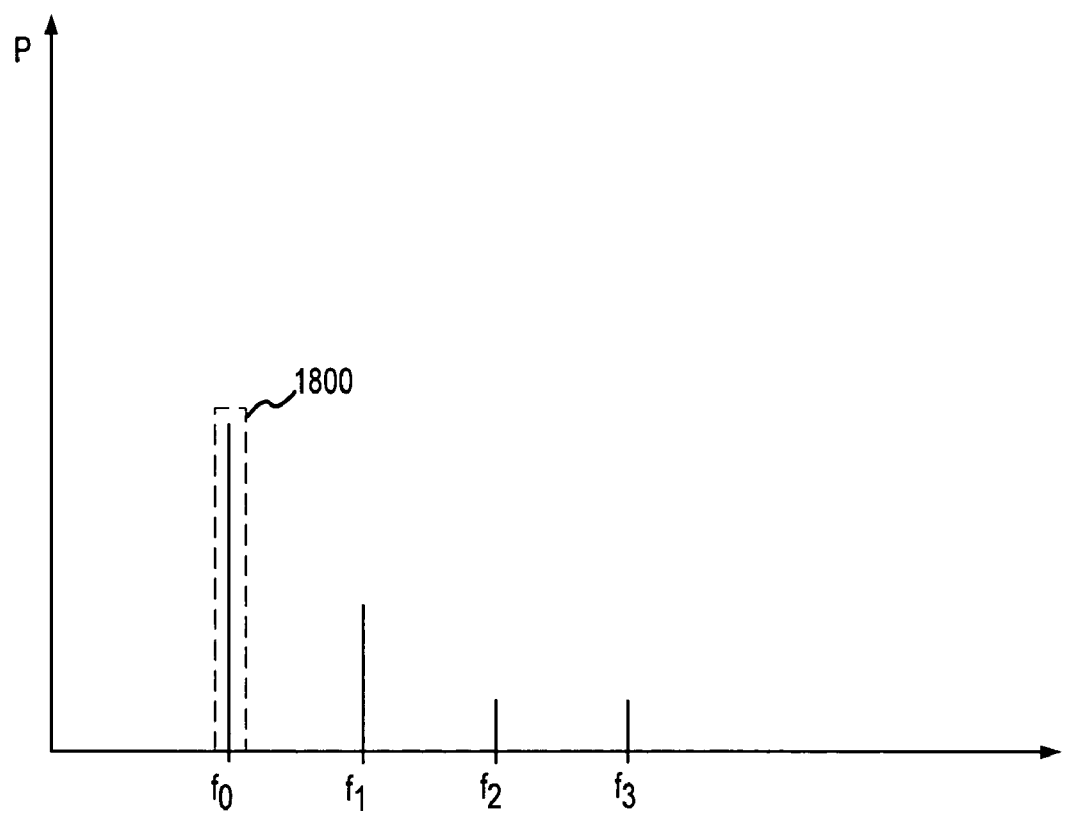
FIG. 18 is a respiratory power spectrum illustrating a transfer function of another filter in accordance with the present invention.

As noted above, FIG. 4 illustrates a pleth power spectrum obtained by configuring the oximeter processor to mathematically obtain a Fourier transform of the time domain pleth signal wherein an adaptive filter functions as a band pass filter having a narrow band pass encompassing the fundamental frequency. According to an additional aspect of the present invention, an additional digital filter is used to process the pleth in order to track respiration rate. In particular, the output of the heart rate filter can be processed to provide a respiratory power spectrum as shown in FIG. 18. For example, the oximeter processor can be configured to perform a Fourier transform on the time series of pulse rate values output by the heart rate filter. The resulting respiratory power spectrum includes a frequency peak correlated to the respiration rate designated as $t_0$. The additional peaks shown in the power spectrum of FIG. 18 relate to harmonics thereof or other heart rate variations. An adaptive filter having a transfer function, generally indicated by function 1800, can be used to track the fundamental frequency. Such a filter may be similar to the heart rate filter as described above and is programmed to adaptively track the noted frequency of the respiratory power spectrum which corresponds to respiration rate. The output of this filter is a periodically updated respiration rate value. Alternatively, a static band pass filter may be used to isolate the peak related to respiration and, hence, identify the respiration rate. Such a filter may have a pass band of 0–0.5 Hz or, to accommodate neonatal applications, 0–1.5 Hz.

Figure 19:
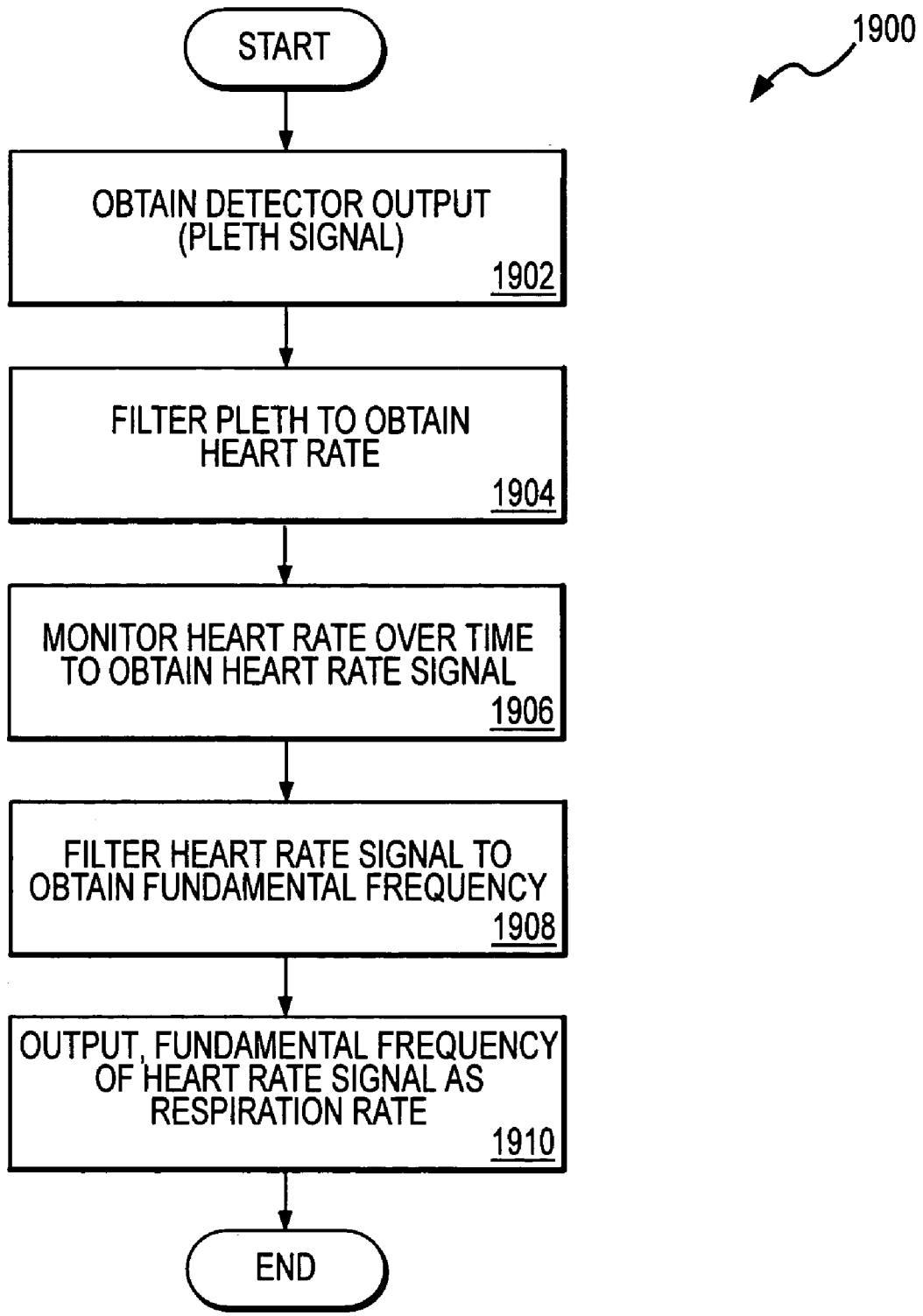
FIG. 19 is a flow chart illustrating a process for using a pleth signal to monitor respiration in accordance with the present invention.

FIG. 19 is a flow chart illustrating a process for determining respiration rate based on pleth signals in accordance with the present invention. The process 1900 is initiated by obtaining a detector output or pleth signal. In the context of a pulse oximeter, this may involve receiving the digital output from an A/D converter that reflects the detector signal, demodulating this signal to obtain individual channel components and selecting a pleth for further processing. The selected pleth may be one of the channels or an optimized pleth based on both of the channel components. The pleth is then filtered (1904) to obtain a time series of heart rate values. These values are monitored (1906) over time to obtain a heart rate signal. The heart rate signal is then filtered (1908) to identify a frequency peak correlated to respiration. The frequency of this peak is then output (1910) as a respiration rate. This respiration rate may be displayed in the display area of a conventional pulse oximeter programmed to provide such information.

Figure 20:
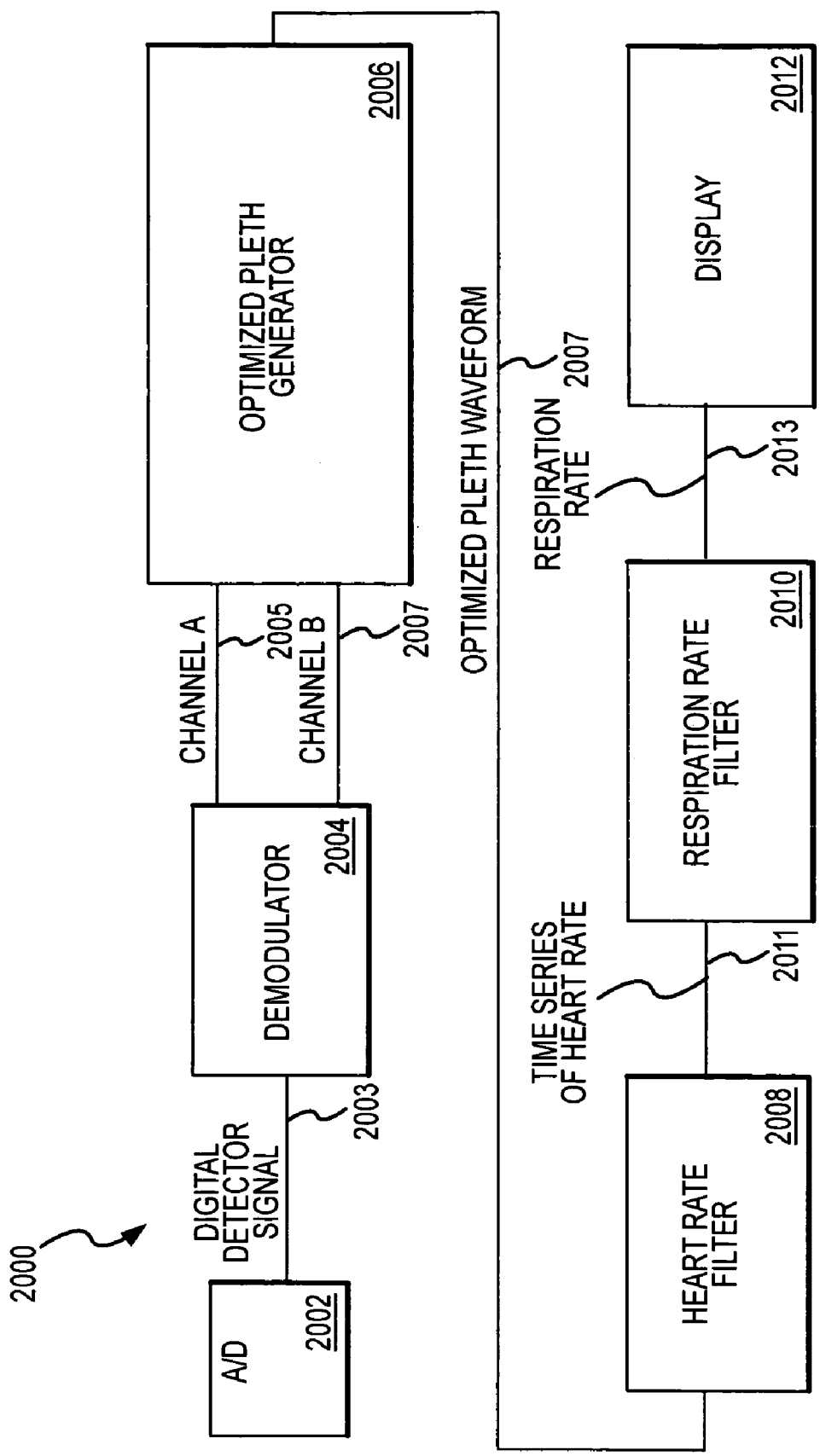
FIG. 20 illustrates a signal processing system in accordance with the present invention.

The corresponding components of a pulse oximeter processing unit are illustrated in FIG. 20. The illustrative unit 2000 includes an A/D converter 2002. The A/D converter receives an analog signal representative of the optical signal received by the pulse oximeter detector. This analog input signal is processed by the converter (2002) to provide a digital detector signal 2003. The digital detector signal 2003 is then processed by demodulator 2004 to provide two separate channel signals designated channel A (2005) and channel B (2007), that may correspond, for example, to the red and infrared channels of the pulse oximeter. These channel signals are then processed by the optimized pleth generator 2006 to provide an optimized pleth waveform 2009. As discussed above, the optimized pleth waveform may correspond to either of the channel signals or a combination thereof. This optimized waveform 2009 is processed by a heart rate filter in order to track the fundamental frequency of the waveform which corresponds to the patient's heart rate. The output from the heart rate filter 2008 is a time series of heart rate values 2011. This time series heart rate values is then processed by a respiration rate filter 2010 which tracks a selected frequency of the corresponding spectrum to determine respiration rate 2013. The patient's respiration rate 2013 may be periodically output to a user via a display 2012.

Figure 21:
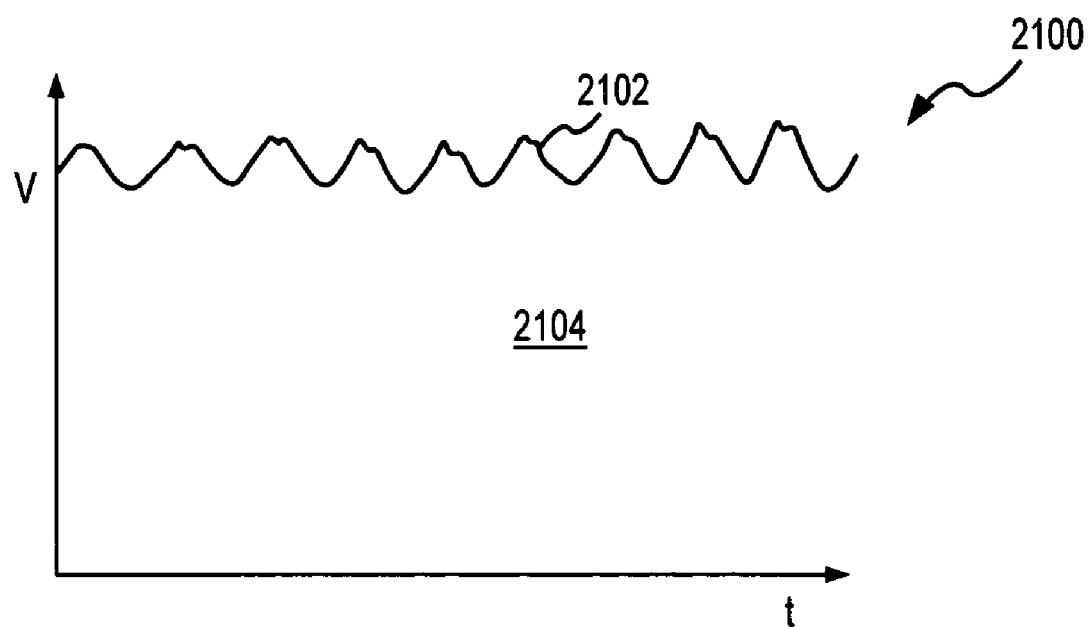
FIG. 21 illustrates the waveform of a pleth that may be used to obtain physiological parameter information in accordance with the present invention.

In another implementation of the present invention, a process is provided for utilizing pleth signals to obtain physiological parameter information related to respiration or the autonomic nervous system. In this regard, FIG. 21 generally illustrates a pleth waveform corresponding to one of two optical channels (e.g., red and infrared) that may be utilized to distinguish Mayer and respiration waves based on wave characteristics other than frequency. As shown, the waveform 2100 generally includes a pulsatile component 2102 having a relatively small magnitude carried by a baseline component 2104 of larger magnitude. The pulsatile component 2102 is the component that is primarily used in pulse oximetry to determine blood oxygenation. This component or the overall signal 2100 may also be used in accordance with the present invention, for example, to monitor pulse rate. The baseline component 2104, sometimes termed the "DC component," includes lower frequency components that reflect important physiological information that may be monitored in accordance with the present invention. In particular, it has been recognized that the baseline component includes a number of sub-components including the Mayer Wave component, the respiration wave component, and other components such as a very low frequency component which is associated with temperature control. The effects related to the respiration wave and the Mayer Wave have particular significance in relation to the implementations of the aspects of present invention described below.

Respiration is believed to have a number of effects on circulation that may be reflected in a pleth. First, the respiratory center in the brain directly influences the vasomotor center, causing respiratory sinus arrhythmia associated with increased heart rate during inspiration and decreased heart rate during expiration. Additionally, the thoracic pressure decreases upon inspiration, increasing the blood content in the chest causing: 1) decreased blood return to the left ventricle, 2) increased blood return to the right ventricle, and 3) decreased venous pressure. Respiration is also believed to produce a rise in arterial pressure during the early part of expiration and a fall in pressure during the remainder of the respiratory cycle. Thus, the prominent effect on arterial pressure is apparently item 1) above. During deep respiration, the blood pressure can rise and fall by as much as 20 mm hg. It has also been recognized in relation to the present invention that the effect of respiration on venous blood outside the thorax is a decrease during inspiration and an increase in venous filling and pressure during expiration.

As noted above, the Mayer Wave is not fully understood. However, the Mayer Wave is believed to relate to an oscillation of the pressure reflex control system attributed mainly to the baroreceptor reflex. The associated cycle is as follows: 1) the baroreceptors sense an increase in pressure and inhibit the sympathetic system which reduces the pressure, 2) this pressure drop causes the baroreceptors to excite the sympathetic nerve system and the blood pressure rises and the cycle starts over. The response of the pressure to the reflex is not instantaneous; it may take a few seconds. The period of the Mayer Wave is generally taken to be between about 6–20 seconds in humans or around 0.05–0.15 Hz. The duration is different in other subjects. The amplitude of the wave can be as high as 40 mm hg, but varies between individuals, decreases with age and increases upon concentration.

Figure 22:
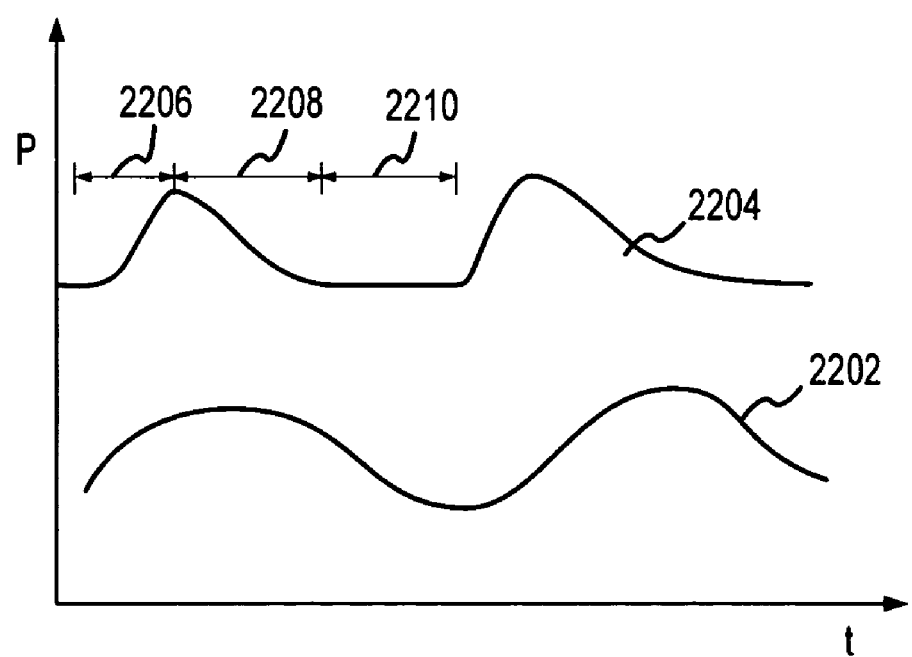
FIG. 22 is a graph illustrating the waveforms of a Mayer Wave and a respiration wave.

The following description concerns distinguishing the Mayer and respiration waves based on a wave characteristic other than frequency. Although any characteristic that yields a cognizable distinction in this regard may be utilized, two apt characteristics are waveform and phase. FIG. 22 illustrates a difference in waveform that may be used to distinguish Mayer Wave effects from respiration wave effects. In particular, FIG. 22 generally illustrates the waveform of a Mayer Wave 2202 and of a respiration wave 2204. As shown, the Mayer Wave 2202 is generally expected to have a simple sinusoidal shape with similar rise times and fall times. The respiration wave 2204 is not. In general, the time period associated with inspiration 2206 is shorter than that of expiration 2208. In addition, there is a significant rest time 2210 during the respiration cycle, especially at low breathing rates. The associated waveform, as reflected in a measured parameter (generally denoted p) such as changes in heart rate or blood pressure, therefore differs from the Mayer waveform as generally shown in FIG. 22. Thus, the Mayer Wave and respiration wave effects can be distinguished by identifying a component of interest in the pleth, monitoring the waveforms of the Mayer Wave and respiration wave using an appropriate measurement parameter, and correlating one of the waveforms to the pleth component of interest.

In this regard, the patient's heart rate and/or blood pressure can be monitored photoplethysmographically or in any other suitable manner. Appropriate methodologies for monitoring measured parameters such as heart rate photoplethysmographically are disclosed above. Thus, in accordance with the present invention, a filter such as a band pass filter can be used to extract a component wave from the pleth, the waveform of the extracted wave can be compared to, e.g., a heart rate waveform to verify that the extracted component wave is a Mayer Wave or a respiration wave, and the extracted component wave can then be analyzed to obtain physiological parameter information. For example, where the extracted component wave is a Mayer Wave, it can be monitored to identify changes of frequency and amplitude that may have diagnostic significance. Where the extracted component wave is a respiration wave, its frequency can be monitored to track respiration rate.

Figure 23:
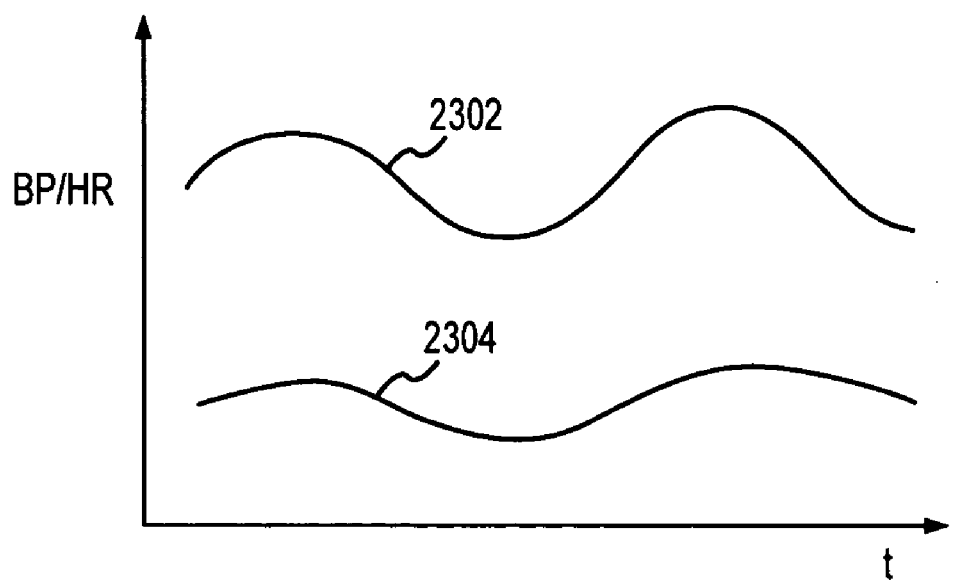
FIG. 23 is a chart illustrating a phase relationship between a blood pressure signal and a heart rate signal corresponding to a Mayer Wave component of a pleth.
Figure 24:
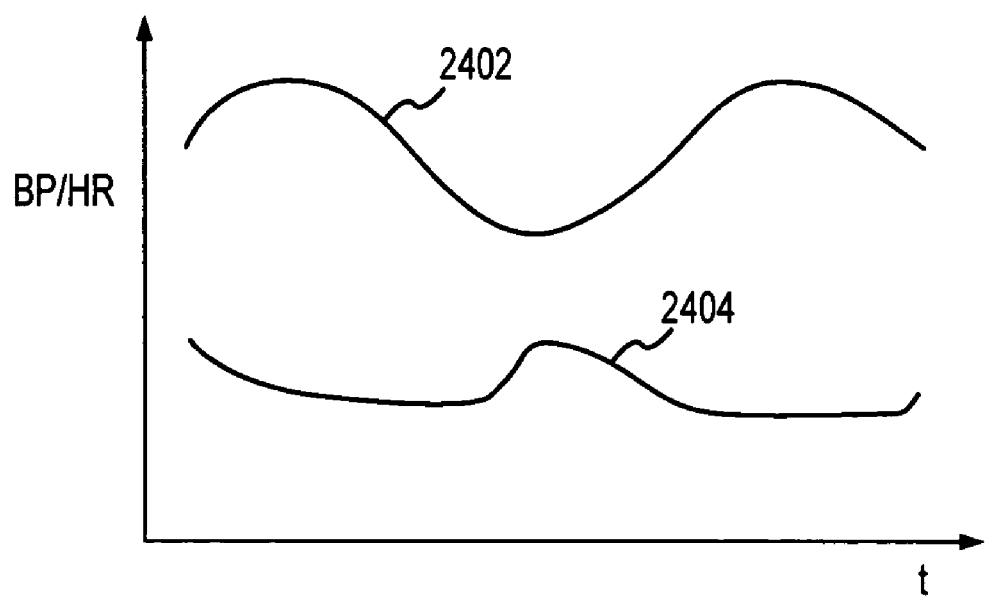
FIG. 24 is a chart illustrating a phase relationship between a blood pressure signal and a heart rate signal for a respiration wave component of a pleth.

The Mayer Wave and respiration wave can also be distinguished based on differing phase relationships of associated parameters. This is illustrated in FIGS. 23 and 24. In particular, FIG. 23 shows the plot of blood pressure 2302 and heart rate 2304 versus time associated with the Mayer Wave. As shown, the Mayer Wave influences blood pressure by a change in heart rate and vaso constriction. In the rising part of the Mayer Wave, both blood pressure and heart rate are increased simultaneously. Thus, the illustrated waves are substantially in phase.

In contrast, FIG. 24 shows the waveforms associated with a respiration wave. Respiration causes a change in blood pressure (as indicated by waveform 2402) because of thoracic pressure differences during inspiration and expiration. Inspiration causes a decrease in left ventricular filling, decreasing the blood pressure (as indicated by waveform 2404). Thus, the illustrated waveforms 2402 and 2404 are out of phase. Accordingly, blood pressure and heart rate changes will generally be out of phase if they are caused by respiration and in phase if they are caused by a Mayer Wave. By acquiring both the changes in blood pressure and heart rate, one can determine the existence of a phase difference, making it possible to distinguish between the respiration and Mayer Wave. Both can be acquired using a pulse oximeter in the following manner:

1. The blood pressure changes can be monitored by acquiring the pleth, which is related to the amount of blood present in the finger, which is directly proportional to the blood pressure. Acquiring the pleth and filtering out unwanted components such as the very low frequencies and the heart rate will give the variation in blood volume, and thus pressure, of the Mayer and respiration waves. The signals corresponding to one or more channels of the pulse oximeter can be used in this regard.

2. The changes in heart rate can be determined by detecting the pulses in the unfiltered plethysmographic signal and determining the time between them. The heart rate will change due to respiration and the Mayer Wave. Thus, an effect of interest can be identified based on appropriate processing, e.g., mathematical or spectral analysis of the pleth. Once this effect or component of interest is identified, corresponding heart rate and blood pressure waveforms can be obtained as described above. Analysis of these waveforms with regard to the phase relationships therebetween yields information as to whether the effect under analysis is associated with the Mayer Wave or the respiration wave. It will be appreciated that, although this process has been illustrated graphically to facilitate a better understanding, the associated methodology can be readily implemented in software or other processing components. Finally, once an effect is thereby distinguished, it can be used to obtain physiological parameter information. For example, as noted above, the respiration wave reflects the respiratory cycle. Once the pleth baseline signal is resolved into its Mayer Wave and respiration wave components, the respiration wave component can be analyzed to obtain respiration rate, e.g., based on identification of successive waveform peaks to obtain the period of respiration or based on spectral analysis/filtering (e.g., involving a Fast Fourier Transform to obtain the fundamental frequency of respiration wave).

Figure 25:
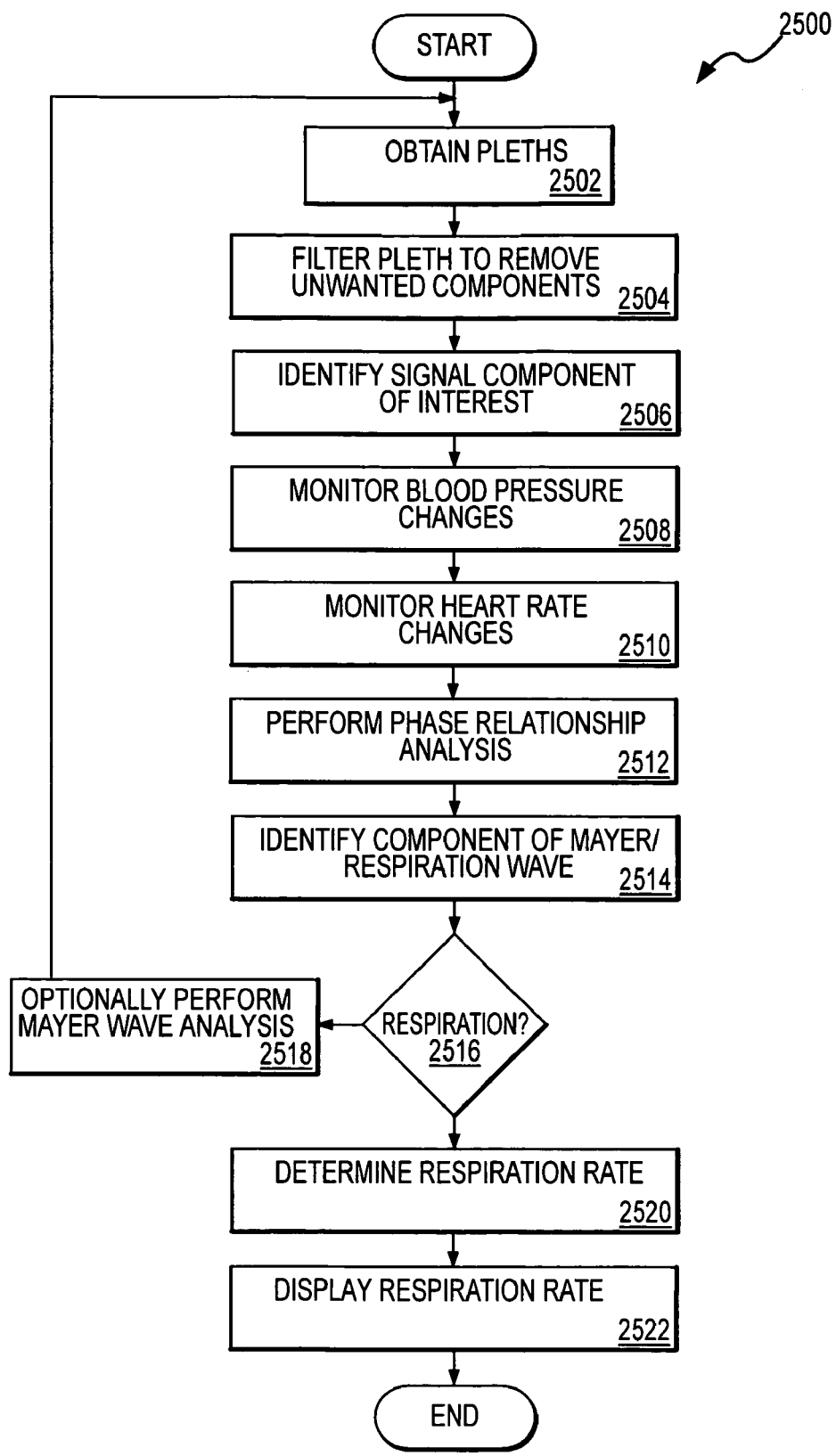
FIG. 25 is a flow chart illustrating a process for obtaining physiological parameter information based on distinguishing an effect associated with a Mayer Wave from an effect associated with a respiration wave in accordance with the present invention.

The associated process 2500 may be summarized by reference to the flow chart of FIG. 25. The process 2500 is initiated by obtaining (2502) one or more pleths for analysis. The present invention may be implemented in connection with a conventional pulse oximeter. In this regard, a pleth corresponding to one of the red and infrared channels, e.g., whichever signal appears to have a better signal to noise ratio, or a composite signal may be utilized. This pleth may then be filtered (2504) to remove unwanted components. For example, the pulsatile component may be separated from the pleth baseline component by one or more band pass filters, high pass filters, low pass filters, or other hardware or software components. In this regard, it is noted that the pulsatile component will generally have a higher frequency that can be readily distinguished from the pleth baseline component including the Mayer Wave and respiration wave.

Once the pleth has been filtered, an effect of interest may be identified (2506) based on analysis of the filtered pleth baseline component. For example, a mathematical or spectral analysis may be used to resolve the pleth baseline signal into two primary components. Then, blood pressure changes may be monitored (2508) relative to the identified effect using the filtered pleth (pleth baseline component). Heart rate may be monitored (2510) using the unfiltered pleth or the pulsatile component. Using the resulting blood pressure and heart rate signals, an analysis is performed (2512) to identify a phase relationship associated with the pleth component of interest. The pleth component of interest is thereby identified (2414) as relating to the respiration wave or the Mayer Wave based on the phase relationship. If the component is identified as being associated with the respiration wave (2516), then the respiration rate may be determined (2520) based on a period measurement or primary frequency analysis. In this regard, the frequency band of interest will generally be 0–0.5 Hz for adult patients but may be extended, e.g., to 0–1.5 Hz for newborns. The resulting respiration rate may then be output (2522) on a display of the pulse oximeter and/or in hard copy form, e.g., on tape. If the identified component is not associated with the respiration wave, then a Mayer Wave analysis may optionally be performed (2518), for example, to monitor a parameter related to the autonomic nervous system and additional pleth signals may be analyzed to identify a respiration wave effect if desired.

Figure 26:
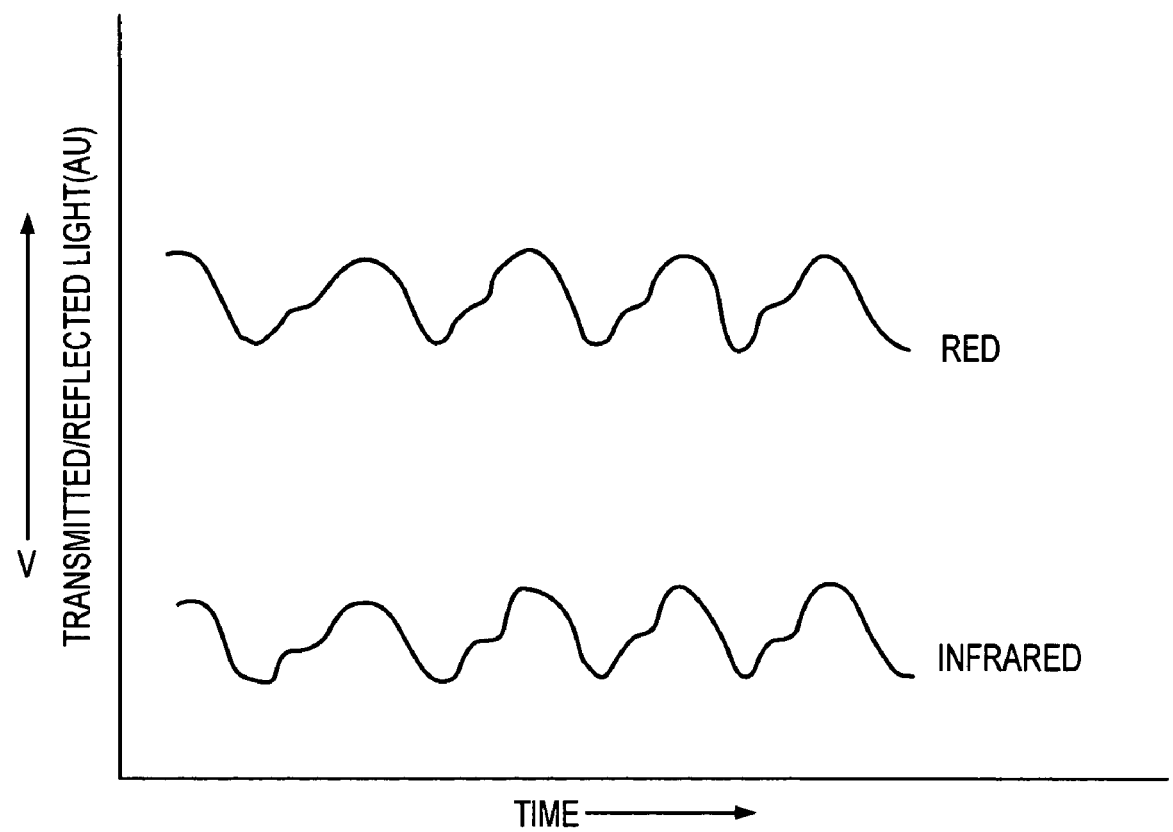
FIG. 26 shows red and infrared channels of an exemplary photoplethysmographic waveform.

According to another aspect of the invention, blood analyte analysis is utilized to differentiate variations in pleth signals caused by respiration waves and Mayer waves. FIG. 26 illustrates red and infrared plethysmographic waveforms representing the signals received by photodetector 18. These waveforms represent a 'raw' (i.e., non-processed) plethysmographic signal which show the intensity or absorption of the light passing through the tissue over time. The pulses in each of the signals represent the rising and falling intensity or attenuation of the light transmitted through or reflected by the tissue caused by the beating of the heart. Each time the heart pulses, the amount of blood in the tissue increases, increasing the amount of light absorbed therein and causing a lowered intensity reading in the plethysmographic signals. As the blood vessels relax between heartbeats, the amount of blood in the tissue is reduced and less light is absorbed. It should be noted that since the red and infrared light pass through substantially the same tissue the photoplethysmographic waveforms for the red channel will be shaped nearly identical to those in the infrared channel, only the amplitude of the red and infrared signal will significantly differ. Additionally, as shown in FIG. 26, the plethysmographic wave for each the red and infrared wavelength is a combination of the AC and DC component and that, as shown, a large base portion of the DC component has been removed such that the amplitude changes of the plethysmographic signal may be better shown. These changes in amplitude correspond with the pulse rate of the patient, which may be readily determined from this raw plethysmographic signal. The AC and DC components of each of the plethysmographic waves may be separated (i.e., filtered) from one another such that these components may be individually monitored.

Figure 27:
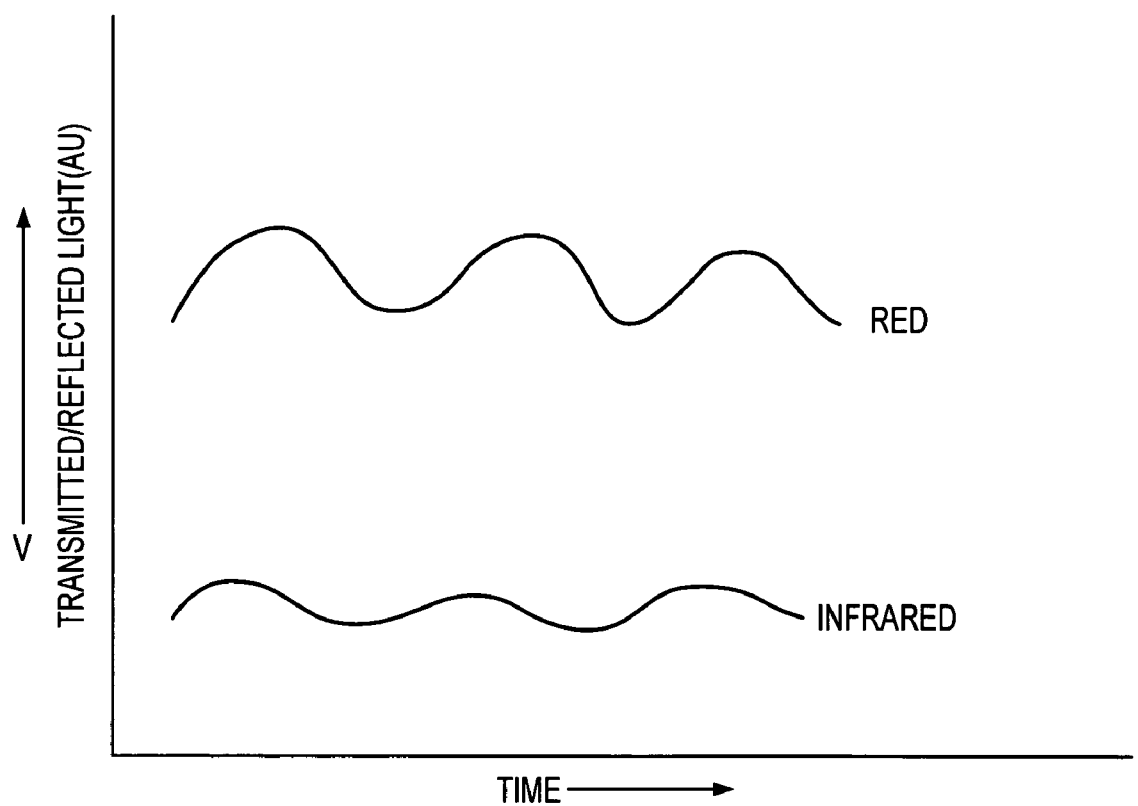
FIG. 27 shows a filtered DC component of a photoplethysmographic waveform for red and infrared channels.

FIG. 27 shows an infrared and red plethysmographic wave in which the AC component has been filtered off, leaving the DC baseline signal. As shown in FIG. 27, the amplitude of the DC signal varies slightly over time even with the pulsatile AC component removed from the plethysmographic signal. This slow change in amplitude is caused by gradual changes in the thickness of the measured tissue (for example, a fingertip), which causes a variance in amount of light absorbed in the tissue. Three non-pulsatile factors are known to cause these slow variances in the DC component of the plethysmographic wave, namely the Mayer wave, respiration, and, to a smaller extent, temperature changes within the tissue. Generally, variance in temperature in the tissue occurs at such a low frequency that it is easily distinguishable from the effects of respiration and the Mayer wave on the plethysmographic wave. However, the Mayer wave, as discussed above, varies on a frequency similar to that of the respiration, which makes it difficult to isolate variances in the raw plethysmographic signal caused solely by the Mayer wave or solely by respiration. In particular, the periodic frequency of the Mayer wave is generally held to be between about six and twenty seconds in humans, or around 0.05 to 0.15 hertz. The Mayer wave can affect the blood pressure within the arteries and veins by as much as 40 milligrams of mercury (40 mm Hg.) However, the strength of the Mayer wave varies between individuals, generally decreases with age, and increases upon concentration. Likewise, the respiratory cycle can cause blood pressure to rise and fall by as much as 20 milligrams of mercury (20 mm Hg.) Additionally, respiration can be expected to occur between 0 and 30 times per minute with a typical adult resting respiration cycle being between 4 and 12 breaths per minute or from about 0.07 to 0.2 hertz.

As the frequencies of the Mayer wave and respiration wave may overlap and have similar effects on blood pressure, their effects on the volume of blood in the tissue may cancel one another out leaving no indication of that they occurred in a raw DC waveform. For example if the Mayer wave causes the baroreceptors to inhibit the sympathetic nerve system which, in turn, reduces blood pressure while a patient is expiring, which causes an increase in pressure, the effects of the two actions may cancel one another out as far as changes in the volume of tissue are concerned. Therefore it becomes difficult if not impossible from a raw plethysmographic signal the effects caused solely by respiration and the effect caused solely by the Mayer wave.

Though similar in their effects on the body, there are differences between the effects of the Mayer wave and respiration. In respiration, the changes in arterial blood pressure and/or venous blood pressure are caused mainly by thoracic pressure changes. As will be appreciated, thoracic pressure changes are caused by the expansion and contraction of the chest cavity (i.e., thorax) during respiration.

Changes in thoracic pressure due to respiration cause accumulation of blood in the vessels inside the chest wall during inspiration (inhaling). The blood pressure change is generally considered to originate from decreased left ventricular filling during inspiration and increased filling during expiration. The venous pressure and thus the venous filling, changes as a direct result of the sucking of blood towards the chest during inspiration and the expulsion of blood from the chest during expiration. This sucking of blood into the chest causes a change in the amount of venous blood in the tissue but does not affect the amount of arterial blood in the tissue. Therefore, respiration causes a variation in the ratio of arterial blood over venous blood in the tissue. In contrast the variation in arterial blood pressure, heart rate and/or vasoconstriction caused by the Mayer wave, has no independent effect on venous blood in relation to arterial blood. In fact, changes in heart rate, blood pressure, and/or vasoconstriction generally affect both the arterial and venous blood in approximately the same way, keeping their relative amounts (i.e., ratio) more or less constant. Therefore, the Mayer wave does not affect the ratio of arterial blood over venous blood in the tissue. Accordingly, by monitoring this ratio for changes over a frequency corresponding with respiration, respiration may be monitored using a pulse oximeter.

The ratio of venous blood to arterial blood is difficult or substantially impossible to measure from the raw plethysmographic signal, therefore, in order to determine this ratio the raw signal must be processed. Assuming the oxygen saturation of the incoming blood and oxygen consumption in the tissue are constant, the ratio of arterial blood over venous blood will be proportional to the oxyhemoglobin over the de-oxyhemoglobin ($HbO_2$/Hb) concentration ratio of the tissue as a whole since, typically, arterial blood is oxygen rich and venous blood is oxygen depleted. Therefore, changes in the arterial blood over venous blood ratio can be monitored by measuring changes in the above ratio. For example, the $HbO_2/Hb$ ratio will rise during inspiration and fall during expiration over a cycle frequency between 0 and 1.5 hertz.

Derivation of an Algorithm for Monitoring $HbO_2/Hb$ in the Tissue as a Whole:

The microprocessor uses the separated DC component of the measured signals to calculate the ratio of oxygenated versus deoxygenated blood. By using only the DC component of the plethysmographic signal, the oxygenated versus de-oxygenated blood ratio will be calculated for the tissue as a whole. Using the Lambert-Beer law, the absorption of light with a first wavelength $\lambda_1$ and an absorption coefficient $\alpha_1$ is as follows:

$$\left[\log \frac{I}{I_o}\right]_{\lambda 1} = -[\alpha_{1HbO2}(HbO_2) + \alpha_{1Hb}(Hb)]L \quad (1)$$

solving for the $HbO_2/Hb$ ratio:

$$\frac{HbO_2}{Hb} = \frac{-1}{\alpha_{1HbO2}L(Hb)}\left[\log \frac{I}{I_o}\right]_{\lambda 1} - \frac{\alpha_{1Hb}}{\alpha_{1HbO2}} \quad (2)$$

For a second wavelength $\lambda_2$ and an absorption coefficient $\alpha_2$:

$$\frac{HbO_2}{Hb} = \frac{-1}{\alpha_{2HbO2}L(Hb)}\left[\log \frac{I}{I_o}\right]_{\lambda 2} - \frac{\alpha_{2Hb}}{\alpha_{21HbO2}} \quad (3)$$

As will be appreciated, the length will be the same for each equation since both wave lengths of light travel through the same portion of tissue. Rearranging the above equation and solving:

$$\frac{-1}{L(Hb)} = \left\{\frac{HbO_2}{Hb} + \frac{\alpha_{2Hb}}{\alpha_{2HbO2}}\right\} \bigg/ \left\{\frac{1}{\alpha_{2HbO2}}\left(\log\frac{I}{I_o}\right)_{\lambda 2}\right\} \quad (4)$$

Substituting this value into the equation (2) and reducing:

$$\frac{HbO_2}{Hb} = \frac{\alpha_{2Hb}Q - \alpha_{1Hb}}{\alpha_{1HbO2} - \alpha_{2HbO2}Q} \quad (5)$$

Where $$Q = \log\left(\frac{I}{I_o}\right)_{\lambda 1} \bigg/ \log\left(\frac{I}{I_o}\right)_{\lambda 2} \quad (6)$$

Allowing $\lambda_1$ to be red light and $\lambda_2$ to be infrared light, the final result is:

$$\frac{HbO_2}{Hb} = \frac{\alpha_{1RHb}Q - \alpha_{redHb}}{\alpha_{redHbO2} - \alpha_{1RHbO2}Q} \quad (7)$$

where:

$$Q = \log\left(\frac{I}{I_o}\right)_{red} \bigg/ \log\left(\frac{I}{I_o}\right)_{1R} \quad (8)$$

Practical Algorithm to Calculate $HbO_2/Hb$ in the Tissue as a Whole:

Because $I_o$ is generally unknown, Q is not calculated directly. Rather, to determine the ratio of oxyhemoglobin to de-oxyhemoglobin the ratio is expressed in terms which may be measured. A method used in arterial blood saturation (i.e., the AC component) calculations to solve this problem is differential absorption. In differential absorption calculations, another representation of Beer' law is used:

$$I = I_o \exp(-\epsilon d) \quad (9)$$

where $\epsilon$ is the extinction coefficient (i.e., color) of the blood and d is the volume of arterial blood. Again we have $I_o$, which is unknown, however by taking the derivative of the above equation the change in intensity over the measured intensity can be determined:

$$\frac{\Delta I}{I} \approx -\varepsilon \cdot \Delta d \quad (10)$$

As the change in the amount of arterial blood ($\Delta d$) is the same for both wavelengths it will cancel out in subsequent calculations and need never be directly measured. However, since the DC component is used $\Delta d$ is not the change in arterial blood due to pulse, but the slow change in the tissue volume due to respiration and the Mayer wave.

The Ratio of Ratios is a variable used in calculating blood oxygen saturation levels in the blood of a patient and may be calculated using instantaneous differential values or peak-to-trough measurements of the red and infrared waveforms. Instantaneous differential values are determined in relation to two or more proximate samples for each channel. Peak-to-trough measurements are obtained by taking the natural logarithm of the ratio of the peak value of the red plethysmographic signal divided by the valley measurement of the red plethysmographic signal. The aforementioned value is then divided by the natural logarithm of the ratio of the peak value of the infrared plethysmographic signal divided by the value of the valley measurement of the infrared plethysmographic signal, or vice versa. In either case, the signals may be measured several times over a given time period and averaged or regression analysis may be performed to obtain the desired ratio of ratios. However, when using differential absorption, the same Ratio of Ratios may be expressed as:

$$R = \left(\frac{\Delta I}{I}\right)_{\lambda 1} \bigg/ \left(\frac{\Delta I}{I}\right)_{\lambda 2} \quad (11)$$

Therefore, R can be derived by taking the derivative of the Beer Lambert Function without the use of logarithms. Plugging in the differential absorption as $\Delta I/I = \epsilon \Delta d$ for each wavelength (change in volume ($\Delta d$) is the same for both wavelengths and therefore cancels) and assuming $HbO_2 + Hb = 1$, leads to:

$$R = \frac{\varepsilon_1}{\varepsilon_2} = \frac{\varepsilon_{1HbO2}(HbO_2) + \varepsilon_{1Hb}(Hb)}{\varepsilon_{2HbO2}(HbO_2) + \varepsilon_{2Hb}(Hb)} \quad (12)$$

Rearranging and solving the equation:

$$\frac{HbO_2}{Hb} = \frac{\varepsilon_{1Hb} - R\varepsilon_{2Hb}}{R\varepsilon_{2HbO2} - \varepsilon_{1HbO2}} \quad (13)$$

As will be appreciated, all the variables in equation (13) may be determined by processing the plethysmographic signals that pass through the tissue in any of several ways known to those skilled in the art. For example, the extinction coefficients may be determined (using logarithms or derivatives) to solve equation (9) for each wavelength as taught by Mortz U.S. Pat. No. 5,934,277. Alternatively, the processor may store look-up tables that contain extinction curves for RHb and $HbO_2$ versus the center wavelengths of the light emitted through the patient's tissue as taught by Jarman U.S. Pat. No. 5,842,979. The Ratio of Ratios may be calculated using the natural logarithmic method described above using the peaks and valleys of the DC components of the plethysmographic signals. By monitoring the resulting value of equation (13) over a predetermined time period (i.e., frequency) for cyclical variations, it is possible to monitor respiration using plethysmographic signals. For example, the resulting value may be plotted versus time such that a respiratory wave may be produced.

Figure 28:
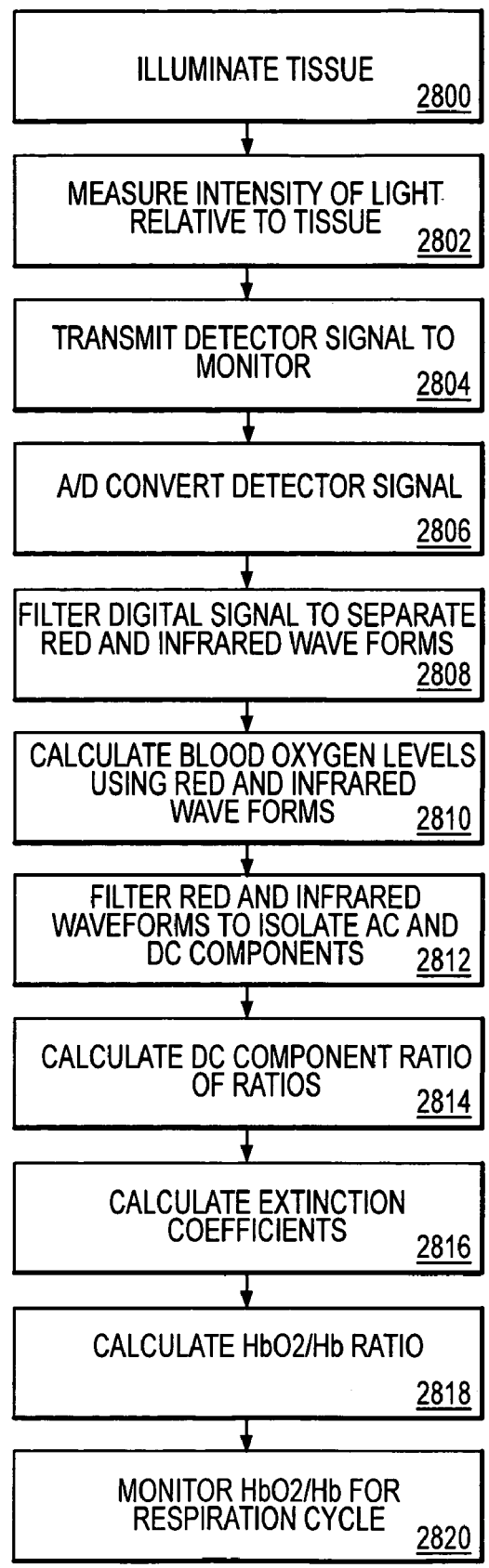
FIG. 28 is a flow chart illustrating a method for monitoring respiration utilizing blood analyte ratios in accordance with the present invention.

Referring to FIG. 28, a method of monitoring respiration with a pulse oximeter according to the present invention is set forth. As described above, the first step is to illuminate (2800) the tissue of the subject with a plurality of light signals emitted at different corresponding centered wavelengths. In order to determine the volume and/or the color of the blood in the tissue at least two light sources having different centered wavelengths are utilized. Preferably a first light source will have a first wavelength in infrared range and a second light source will have a second wavelength in the red range. The intensity of the light transmitted through or reflected from the tissue under test is measured (2802) through the use one or more photodetectors which produces a signal corresponding to the intensity of the light it receives. This signal may comprise a single multiplexed signal which represents the intensity of both the first and second wavelengths of light transmitted relative to the tissue or separate signals for each wavelength. This intensity measurement (i.e., detector signal), represented in an analog form, is transmitted (2804) to the plethysmographic monitor. Once received by the monitor, the analog signal is converted (2806) into a digital equivalent using an analog to digital (A/D) converter, which may be part of the probe interface with the monitor. The resulting digital signal(s) is stored by the monitor and manipulated by the processor according to instructions stored therein. In particular, the digital signal is filtered (2808) such that the infrared and red waveforms are separated from one another so they may be individually monitored. Once the red and infrared waveforms are separated from one another, the Blood Oxygen Saturation Level of the tissue may be calculated (2810) by calculating the Ratio of Ratios from the peaks and valleys of the red and infrared waveforms as known in the art. More preferably, the Ratio of Ratios may be calculated based on instantaneous differential values and multiple values may be analyzed in a regression analysis to obtain a result related to blood oxygenation. The red and infrared waveforms are further filtered (2812) to separate the AC and DC components contained therein. Once the DC component of both the red and infrared waveforms is available, the processor may begin taking samples over predetermined time period from these waveforms. From these sample or data points, the processor is able to calculate (2814) the DC component Ratio of Ratios by taking an average of the peak and valley values of the red and infrared DC waveforms or other differential values over a predetermined time period and performing logarithmic computations with these values. In addition, the processor is configured to calculate (2816) the extinction coefficients for both the red and infrared waveforms for the $HbO_2$ and the RHb. Once a DC component Ratio of Ratios and extinction coefficients are calculated, the processor calculates (2818) the $HbO_2$/Hb ratio and produces an output indicative thereof. For example, the monitor may plot this ratio versus time such that a respiration wave is produced. The respiration wave in this instance will comprise a cyclical waveform increasing and decreasing with the respiration cycle. Accordingly each peak to peak or valley to valley measurement would correspond with a full respiratory cycle that may be easily monitored (2820) along with blood oxygen saturation levels typically taken by the pulse oximeter. It will be appreciated that other waveform related analysis may be utilized to obtain respiration information.

While various embodiments of the present invention and then described in detail, is apparent to further modifications and adaptations of the invention will occur to those skilled in the art. However, it is to be expressly understood that such modifications and adaptations are within spirit in scope of the present invention.

The invention claimed is:

1. A method for use in non-invasively monitoring a physiological parameter of a patient, comprising the steps of:
    obtaining a time-based photoplethysmographic ("pleth") signal that is modulated based on interaction of a transmitted optical signal with blood of said patient, wherein said pleth signal includes at least a first component associated with the operation of the patient's respiratory system and a second Mayer wave component associated with the patient's autonomic nervous system;
    transforming said time-based pleth signal into a frecquency domain to obtain spectral information including information associated with said first component and said second Mayer wave components;
    processing said spectral information to distinguish an effect associated with one of said first component and second Mayer wave component from an effect associated with the other of said components; and
    using said distinguished effect to monitor said physiological parameter.

2. A method as set forth in claim 1, further comprising: providing an output related to said Mayer wave.

3. A method as set forth in claim 2, wherein said step of providing an output comprises providing a graphical output that shows at least one of an amplitude and a frequency of the Mayer Wave.

4. A method as set forth in claim 1, further comprising monitoring one of said amplitude and said frequency over time to detect a variation of interest.

5. A method as set forth in claim 1, wherein said step of processing comprises extracting information regarding at least one of an amplitude and a frequency of a Mayer Wave.

6. A method as set forth in claim 5, wherein said step of processing comprises filtering the spectral information to extract information regarding the Mayer Wave.

7. A method as set forth in claim 6, wherein said step of filtering comprises band pass filtering the spectral information using a frequency band that passes a spectral peak of said spectral information located between about 0.05 Hz and 0.5 Hz.

8. A method as set forth in claim 1, further comprising: processing said spectral information to identify a variation in blood volume.

9. A method as set forth in claim 1, wherein said step of processing comprises first analyzing said spectral information to obtain heart rate information.

10. A method as set forth in claim 9, wherein said step of processing further comprises monitoring said heart rate information over time to obtain a time series of heart rate values.

11. A method as set forth in claim 9, wherein said step of processing further comprises second analyzing said heart rate information to obtain information regarding heart rate variability.

12. A method as set forth in claim 9, wherein said heart rate information comprises a time series of heart rate values and said step of processing further comprises filtering said time series of heart rate values to identify a low frequency variability therein.

13. A method as set forth in claim 12, wherein said low frequency variability is in the range between about 0.05 Hz and 0.5 Hz.

* * * * *